(12) United States Patent
Blanchard et al.

(10) Patent No.: US 9,523,623 B2
(45) Date of Patent: Dec. 20, 2016

(54) METHODS FOR TESTING A HONEYCOMB FILTER

(71) Applicants: Aisha Price Blanchard, Horseheads, NY (US); Julie Charmaine Frey, Corning, NY (US); Patrick Michael Gargano, Corning, NY (US); Ameya Joshi, Horseheads, NY (US); Konstantin Vladimirovich Khodosevich, Saint Petersburg (RU); William Paul Ryszytiwskyj, Corning, NY (US); John Paul Bir Singh, Painted Post, NY (US)

(72) Inventors: Aisha Price Blanchard, Horseheads, NY (US); Julie Charmaine Frey, Corning, NY (US); Patrick Michael Gargano, Corning, NY (US); Ameya Joshi, Horseheads, NY (US); Konstantin Vladimirovich Khodosevich, Saint Petersburg (RU); William Paul Ryszytiwskyj, Corning, NY (US); John Paul Bir Singh, Painted Post, NY (US)

(73) Assignee: Corning Incorporated, Corning, NY (US)

( * ) Notice: Subject to any disclaimer, the term of this patent is extended or adjusted under 35 U.S.C. 154(b) by 500 days.

(21) Appl. No.: 13/687,759

(22) Filed: Nov. 28, 2012

(65) Prior Publication Data

US 2014/0144212 A1    May 29, 2014

(51) Int. Cl.
*G01N 15/08* (2006.01)
*G01M 3/20* (2006.01)
*B01D 46/24* (2006.01)

(52) U.S. Cl.
CPC ............ *G01M 3/20* (2013.01); *B01D 46/2418* (2013.01); *G01N 15/082* (2013.01); *G01N 2015/084* (2013.01)

(58) Field of Classification Search
CPC ............ B01D 46/2418; B01D 2273/18; B01D 63/066; B01D 71/024; B01D 65/102; F01N 3/022; C04B 38/0006; G01N 15/08; G01N 15/082; G01N 15/084; G01N 2015/084; G01N 21/95692; G01M 3/20
(Continued)

(56) References Cited

U.S. PATENT DOCUMENTS 2,229,235 A * 1/1941 Adams ......................... 405/131
4,319,840 A    3/1982 Kondo et al. ................. 356/241
(Continued)

FOREIGN PATENT DOCUMENTS

EP    2415510 A1    8/2012    ............. B01D 39/20
JP    2002195931    7/2002
(Continued)

OTHER PUBLICATIONS

International Search Report and Written Opinion, Dated Mar. 14, 2014, International Application No. PCT/US2013/071399, International Filing Date Nov. 22, 2013.

*Primary Examiner* — John Fitzgerald
*Assistant Examiner* — Truong Phan
(74) *Attorney, Agent, or Firm* — Joseph M. Homa; Charles A. Greene

(57) ABSTRACT

Methods of testing a honeycomb filter include the step of maintaining an average temperature of the honeycomb filter and/or fog within a range of from about 10° C. to about 30° C. and flowing a fog with moisture droplets into the honeycomb network of channels at the first end portion of the
(Continued)

honeycomb filter, the fog including a relative humidity of at least 80%. In further examples, the moisture droplets include a mean droplet size of from about 1 micron to about 25 microns.

32 Claims, 16 Drawing Sheets

(58) Field of Classification Search
USPC .............................. 73/38, 865.6, 40, 40.7, 73
See application file for complete search history.

(56) References Cited

U.S. PATENT DOCUMENTS

| | | |
|---|---|---|
| 5,411,682 A | 5/1995 | Nagashima ............... 264/36 |
| 5,640,236 A | 6/1997 | Nagashima ............... 356/237 |
| 6,666,070 B1 | 12/2003 | Hagg et al. |
| 7,012,678 B2 | 3/2006 | Enomoto et al. ........ 356/237.1 |
| 7,410,528 B2 | 8/2008 | Rae et al. |
| 7,520,918 B2 | 4/2009 | Zoeller, III |
| 7,648,549 B2 | 1/2010 | Gargano et al. |
| 7,755,750 B2 | 7/2010 | Kato |
| 9,038,439 B2 | 5/2015 | Citriniti et al. |
| 9,134,218 B2 | 9/2015 | Blanchard et al. |
| 2007/0222724 A1 | 9/2007 | Ueno et al. |
| 2007/0238191 A1* | 10/2007 | Gargano et al. ............ 436/164 |
| 2008/0000206 A1* | 1/2008 | DaCosta ............ B01D 46/0024 55/523 |
| 2011/0048109 A1* | 3/2011 | Suman ............... B01D 46/2418 73/38 |
| 2012/0017555 A1 | 1/2012 | Iwasaki et al. ............. 55/488 |
| 2012/0247224 A1* | 10/2012 | Miyashita ............ B01D 65/10 73/861 |

FOREIGN PATENT DOCUMENTS

| | | | |
|---|---|---|---|
| JP | 2009115655 | 5/2009 | |
| WO | WO02082035 A1 | 10/2002 | ............ G01M 3/20 |
| WO | WO2007111014 A1 | 4/2007 | ............ G01N 21/894 |
| WO | WO2007126692 A2 | 11/2007 | ............ F01N 11/00 |
| WO | 2008091496 A2 | 7/2008 | |
| WO | 2012124772 | 9/2012 | |

* cited by examiner

METHODS FOR TESTING A HONEYCOMB FILTER

FIELD

The present disclosure relates generally to methods for testing a honeycomb filter and, more particularly, to methods for testing a honeycomb filter including a predetermined filter temperature, a predetermined fog temperature, a predetermined fog humidity and/or a predetermined mean droplet size of the droplets within the fog.

BACKGROUND

Wall-flow honeycomb filters are commonly used to remove solid particulates from fluids, such as in exhaust gas streams. FIG. 1 illustrates a typical honeycomb filter 100 with an inlet end face 102 for receiving the inlet gas stream, an outlet end face 104 for expelling the outlet gas stream, and an array of generally parallel intersecting porous walls 106 extending longitudinally from the inlet end face 102 to the outlet end face 104. The intersecting porous walls 106 define a honeycomb network of channels 107 including a plurality of inlet cell channels 108 and a plurality of outlet cell channels 110. The outlet cell channels 110 are closed with plugs 112 where they adjoin the inlet end face 102 and open where they adjoin the outlet end face 104. Oppositely, the inlet cell channels 108 are closed with porous plugs (not shown) where they adjoin the outlet end face 104 and open where they adjoin the inlet end face 102. Honeycomb filters 100 are typically secured in a compliant mat and contained in a rigid housing (not shown). Fluid directed at the inlet end face 102 of the honeycomb filter 100 enters the inlet cell channels 108, flows through the interconnecting porous walls 106 and into the outlet cell channels 110, and exits the honeycomb filter 100 at the outlet end face 104.

In a typical cell structure, each inlet channel 108 is bordered on one or more sides by outlet cells 110, and vice versa. The inlet and outlet channels 108, 110 may have a square cross-section as shown in FIG. 1 or may have other cell geometry, e.g., circular, rectangle, triangle, hexagon, octagon, etc. Diesel particulate filters are typically made of ceramic materials, such as cordierite, aluminum titanate, mullite or silicon carbide. When particulates, such as soot found in exhaust gas, flow through the interconnecting porous walls 106 of the honeycomb filter 100, a portion of the particulates in the fluid flow stream is retained by the interconnecting porous walls 106. The efficiency of the honeycomb filter 100 is related to the effectiveness of the interconnecting porous walls 106 in filtering the particulates from the fluid. Filtration efficiencies in excess of 80% by weight of the particulates may be achieved with honeycomb filters. However, filtration efficiency or integrity of a honeycomb filter can be compromised by various defects, such as holes or cracks (such as fissures) and the like in the walls or plugs. Such defects allow the fluid to pass through the filter without proper filtration. Thus, in the manufacture of honeycomb filters, it may be desirable to test the honeycomb filters for the presence of such defects that may affect filtration efficiency or integrity. Honeycombs with detected defects may be repaired, or if irreparable, discarded.

SUMMARY

In a first aspect, methods of testing a honeycomb filter include the step (I) of providing a honeycomb filter including a first end portion and a second end portion along an axis of the honeycomb filter. The honeycomb filter includes a honeycomb network of channels defined by a plurality of intersecting porous walls. The honeycomb network of channels extends along the axis of the honeycomb filter between the first end portion and the second end portion. The method further includes the step (II) of maintaining an average temperature of the honeycomb filter within a range of from about 10° C. to about 30° C. The method still further includes the step (III) of flowing a fog with moisture droplets into the honeycomb network of channels at the first end portion of the honeycomb filter, the fog including a relative humidity of at least 80%. The method further includes the step (IV) of monitoring the second end portion of the honeycomb filter for moisture droplets of the fog exiting the honeycomb network of channels.

In one example of the first aspect, step (II) maintains the average temperature of the honeycomb filter within a range of from about 10° C. to about 25° C., for example, from about 20° C. to about 23° C.

In another example of the first aspect, step (III) flows the fog with a temperature within a range of from about 10° C. to about 30° C., for example from about 10° C. to about 25° C., for example from about 23° C. to about 25° C.

In still another example of the first aspect, step (III) flows the fog with the moisture droplets having a mean droplet size of from about 1 micron to about 25 microns, for example from about 5 microns to about 25 microns.

In another example of the first aspect, step (III) flows the fog at a pressure differential between the first end portion and the second end portion of from about 32 Pa to about 37 Pa.

In still another example of the first aspect, step (III) flows the fog through honeycomb network of channels at a flow rate of from about 0.075 m/sec to about 0.1 msec.

In a second aspect, a method of testing a honeycomb filter comprises the step (I) of providing a honeycomb filter including a first end portion and a second end portion along an axis of the honeycomb filter. The honeycomb filter includes a honeycomb network of channels defined by a plurality of intersecting porous walls. The honeycomb network of channels extends along the axis of the honeycomb filter between the first end portion and the second end portion. The method further includes the step (II) of flowing a fog with moisture droplets into the honeycomb network of channels at the first end portion of the honeycomb filter. The fog includes a temperature within a range of from about 10° C. to about 30° C., and a relative humidity of at least 80%. The method also includes the step (III) of monitoring the second end portion of the honeycomb filter for moisture droplets of the fog exiting the honeycomb network of channels.

In one example of the second aspect, step (II) flows the fog with a temperature within a range of from about 10° C. to about 25° C., for example from about 23° C. to about 25° C.

In another example of the second aspect, step (III) flows the fog with the moisture droplets having a mean droplet size of from about 1 micron to about 25 microns, for example from about 5 microns to about 25 microns.

In still another example of the second aspect, step (III) flows the fog at a pressure differential between the first end portion and the second end portion of from about 32 Pa to about 37 Pa.

In yet another example of the second aspect, step (III) flows the fog through honeycomb network of channels at a flow rate of from about 0.075 m/sec to about 0.1 msec.

The second aspect may be carried out alone or in combination with one or any combination of examples of the second aspect discussed above.

In a third aspect, methods include the step (I) of providing a honeycomb filter including a first end portion and a second end portion along an axis of the honeycomb filter. The honeycomb filter includes a honeycomb network of channels defined by a plurality of intersecting porous walls. The honeycomb network of channels extends along the axis of the honeycomb filter between the first end portion and the second end portion. The method further includes the step (II) of maintaining an average temperature of the honeycomb filter within a range of from about 10° C. to about 30° C. The method also includes the step (III) of flowing a fog with moisture droplets into the honeycomb network of channels at the first end portion of the honeycomb filter, the moisture droplets having a mean droplet size of from about 5 microns to about 25 microns, the fog including a temperature within a range of from about 10° C. to about 30° C. and a relative humidity of at least 80%. The method further includes the step (IV) of monitoring the second end portion of the honeycomb filter for moisture droplets of the fog exiting the honeycomb network of channels.

In one example of the third aspect, the method further includes the step step (III) of flowing the fog at a pressure differential between the first end portion and the second end portion of from about 32 Pa to about 37 Pa.

In another example of the third aspect, step (III) flows the fog through honeycomb network of channels at a flow rate of from about 0.075 m/sec to about 0.1 msec.

BRIEF DESCRIPTION OF THE DRAWINGS

These and other features, aspects and advantages of the claimed invention are better understood when the following detailed description is read with reference to the accompanying drawings, in which:

DETAILED DESCRIPTION

Figure 1:
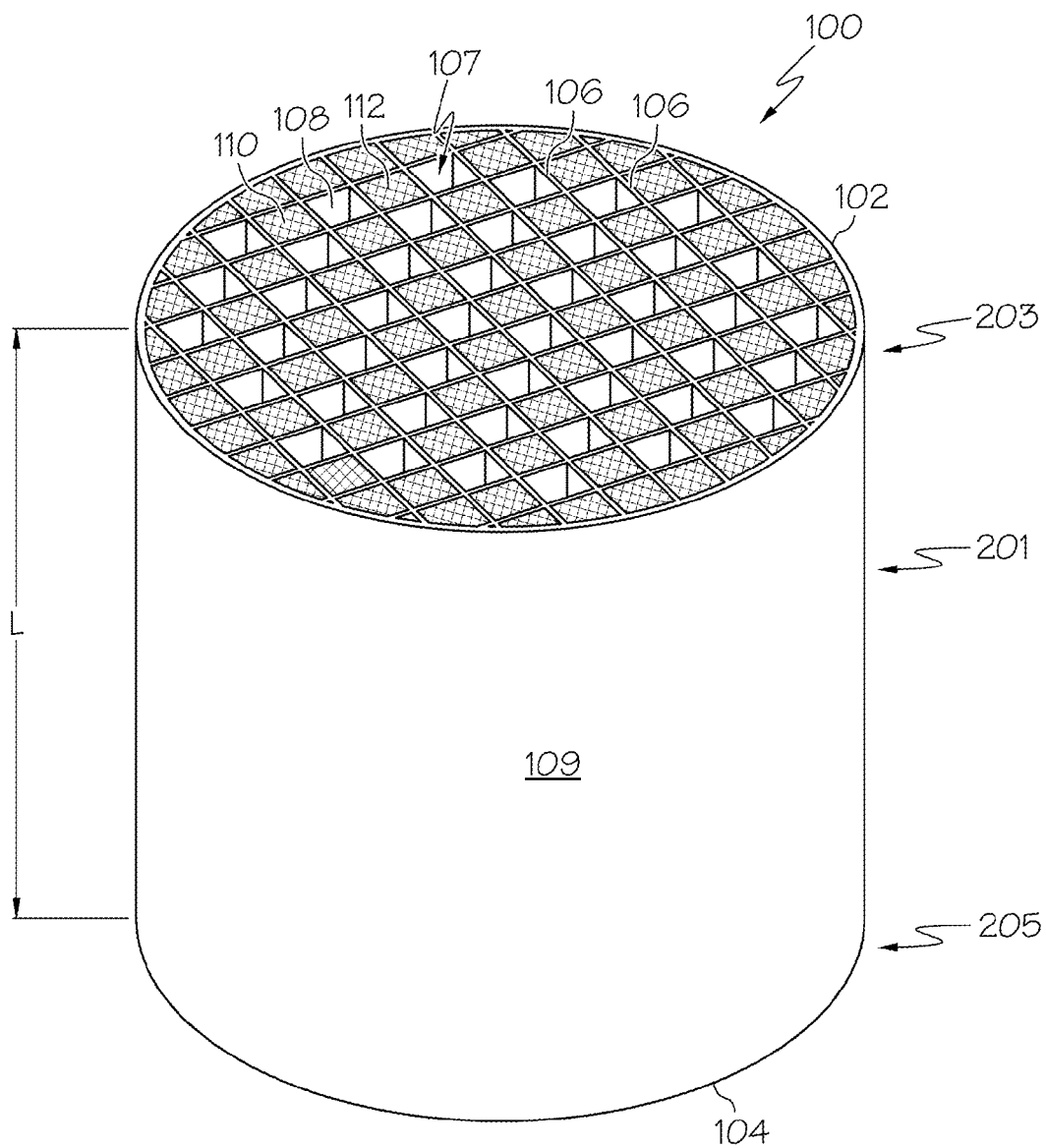
FIG. 1 is a conventional view of a honeycomb filter.

Aspects of the claimed invention will now be described more fully hereinafter with reference to the accompanying drawings in which example embodiments of the claimed invention are shown. Whenever possible, the same reference numerals are used throughout the drawings to refer to the same or like parts. However, the claimed invention may be embodied in many different forms and should not be construed as limited to the embodiments set forth herein. These example embodiments are provided so that this disclosure will be both thorough and complete, and will fully convey the scope of the claimed invention to those skilled in the art.

Referring now to FIGS. 2-8 illustrate one example method of testing a honeycomb filter 100 includes the step of providing a honeycomb filter, such as the conventional honeycomb filter 100 shown in FIG. 1. The honeycomb filter 100 can be provided by manufacturing the honeycomb filter or portions of the honeycomb filter. In further examples, the honeycomb filter can be provided off-the-shelf where the honeycomb filter was produced at a different location and/or purchased for later testing. Testing the honeycomb filters may be desirable to determine if there are cracks or other defects in the honeycomb filter that would interfere with the structural integrity, performance or other characteristics of the filter. Honeycomb filters that pass the testing procedure may then be further processed to provide further characteristics and/or may be mounted within a filter assembly (e.g., diesel particulate filter) for later use.

Figure 2:
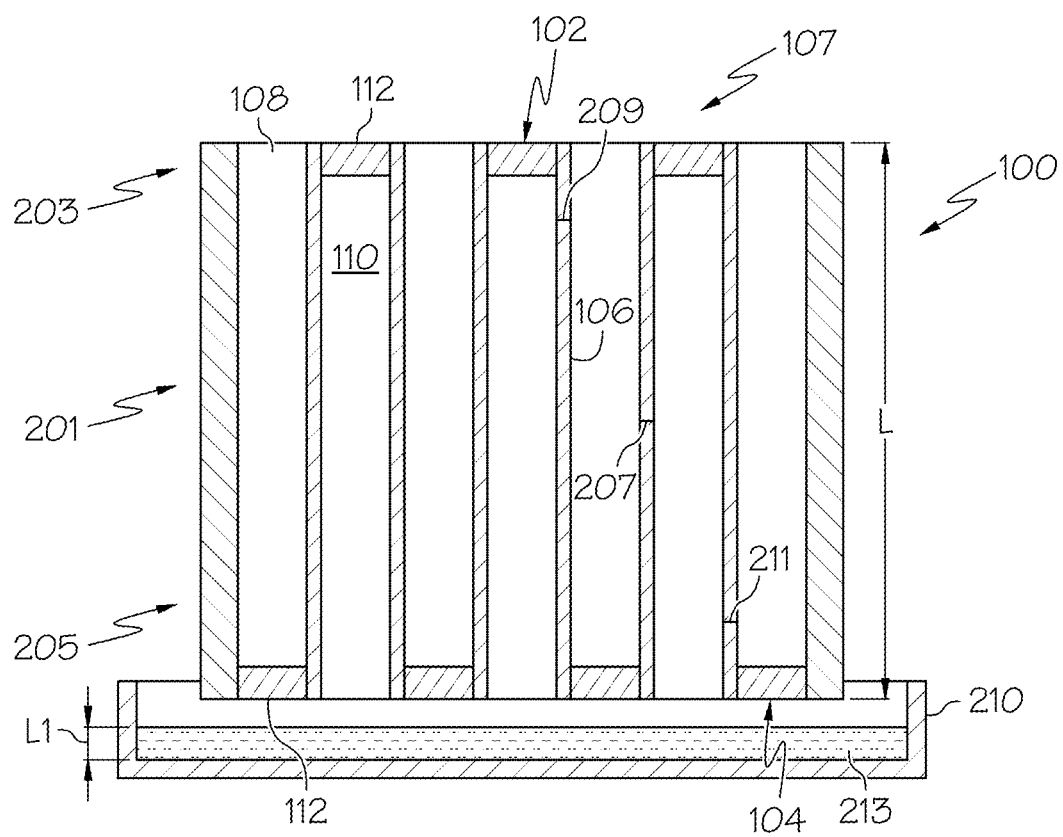
FIG. 2 is a cross sectional view of the honeycomb filter of FIG. 1 prior to wetting the second end portion of the honeycomb filter.

Referring to FIG. 2, the honeycomb filter 100 includes an intermediate portion 201 disposed between a first end portion 203 and a second end portion 205 along a length "L" of the honeycomb filter 100. The honeycomb filter 100 includes the honeycomb network of channels 107 that may include a plurality of inlet cell channels 108 and a plurality of outlet cell channels 110. The honeycomb network of channels 107 is defined by the plurality of intersecting porous walls 106. As shown, in some examples, the plurality of intersecting porous walls 106 may be substantially parallel with respect to one another. As illustrate, the honeycomb network of channels 107 can extend along the length "L" of the honeycomb filter 100 between the first end portion 203 and the second end portion 205.

When testing the honeycomb filter 100, it is desired to locate defects such as holes, cracks (such as fissures) or the like in the porous walls 106 and/or the plugs 112 (e.g., porous plugs). For example, defects may be located in the intermediate portion 201, the first end portion 203 and/or the second end portion 205. For illustration purposes, a first example defect 207 is located in the intermediate portion 201, a second example defect 209 is located in the first end portion 203, and a third example defect 211 is located in the second end portion 205. A nebulizer or other fog generator device may be used to help identify the defects within the honeycomb filter 100 by forcing fog through the filter by generating a pressure drop. Fog not trapped by the porous walls of the honeycomb filter can be monitored as an indicator of a potential defect within the filter. Indeed, rather than being trapped by the porous walls, the fog may freely pass through the defect, thereby short-circuiting the desired path through the porous walls.

Defects within the first end portion 203 and the second end portion 205 may be relatively easier to detect since the fluid dynamic pressure gradient between the channels that acts to push the fog through the porous walls are maximum at the first end portion 203 and the second end portion 205. In contrast, defects within the intermediate portion 201 may be relatively harder to detect since the fluid dynamic pressure gradient between the channels that acts to push the fog through the porous walls may be minimized within the intermediate portion 203 of the honeycomb filter 100.

Defects within the intermediate portion 201 may be more effectively identified by a the method step of wetting at least one of the first end portion 203 and the second end portion 205 to provide at least one wetted end portion, wherein the wetted end portion has a higher degree of wetness than the intermediate portion. Indeed, the step of wetting at least one of the first end portion 203 and the second end portion 205 can increase the sensitivity of the nebulizer or other fog generator device in the intermediate portion 201 of the honeycomb filter 100. It is believed that wetting the end portions acts to at least partially block the flow of air through the wetted end portion(s) by temporarily plugging the pores via capillary forces in the vicinity of the wetted end portions (s). As such, flow through the matrix in the center third of the part may be increased to improve the sensitivity of the nebulizer or other fog generator device to allow more effective identification of defects within the intermediate portion 201 of the honeycomb filter 100.

Figure 3:
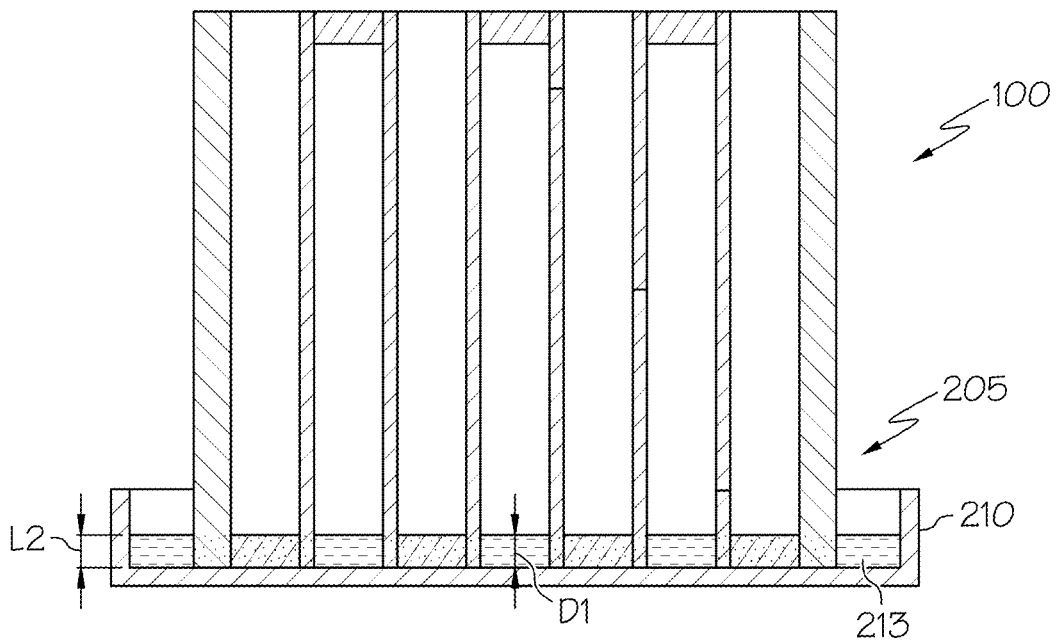
FIG. 3 is a cross sectional view of the honeycomb filter of FIG. 1 while wetting the second end portion of the honeycomb filter.
Figure 4:
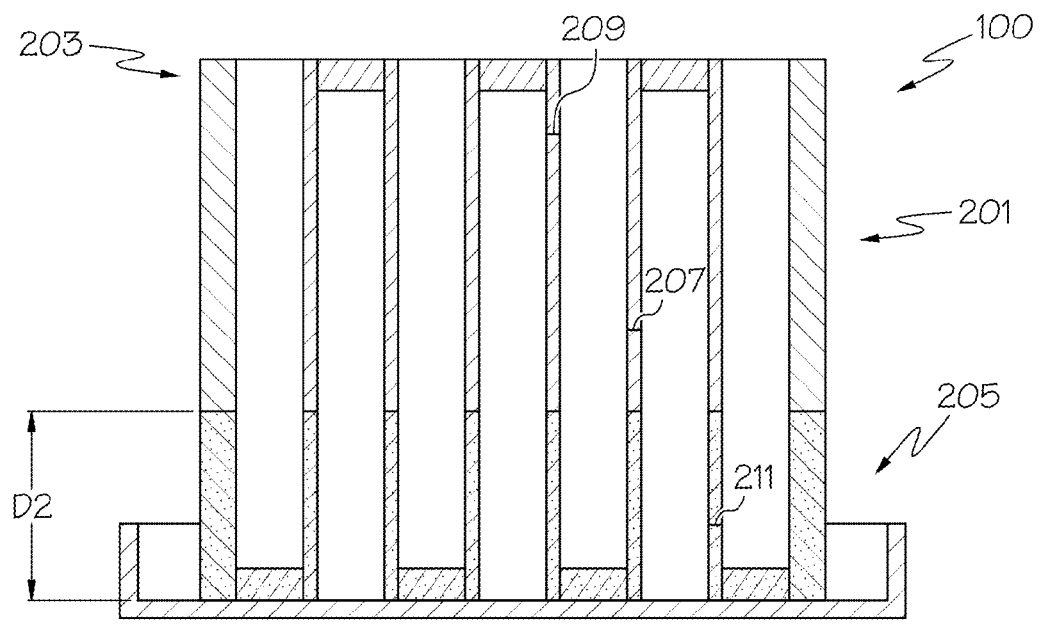
FIG. 4 is a cross sectional view of the honeycomb filter of FIG. 1 after wetting the second end portion of the honeycomb filter.
Figure 5:
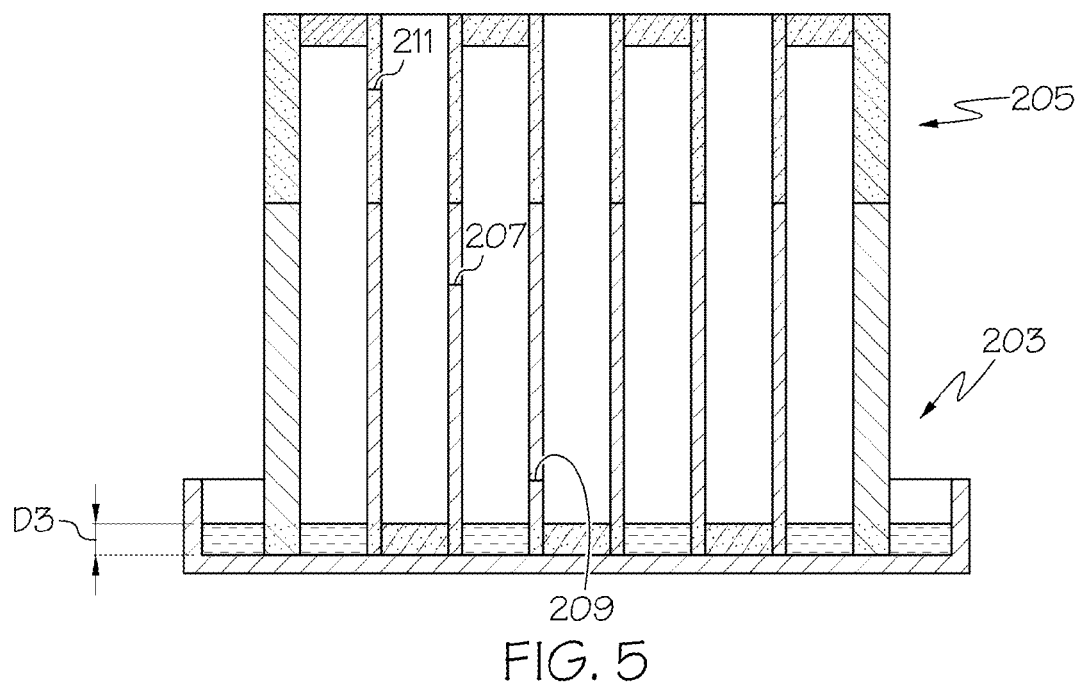
FIG. 5 is a cross sectional view of the honeycomb filter of FIG. 1 while wetting the first end portion of the honeycomb filter.
Figure 6:
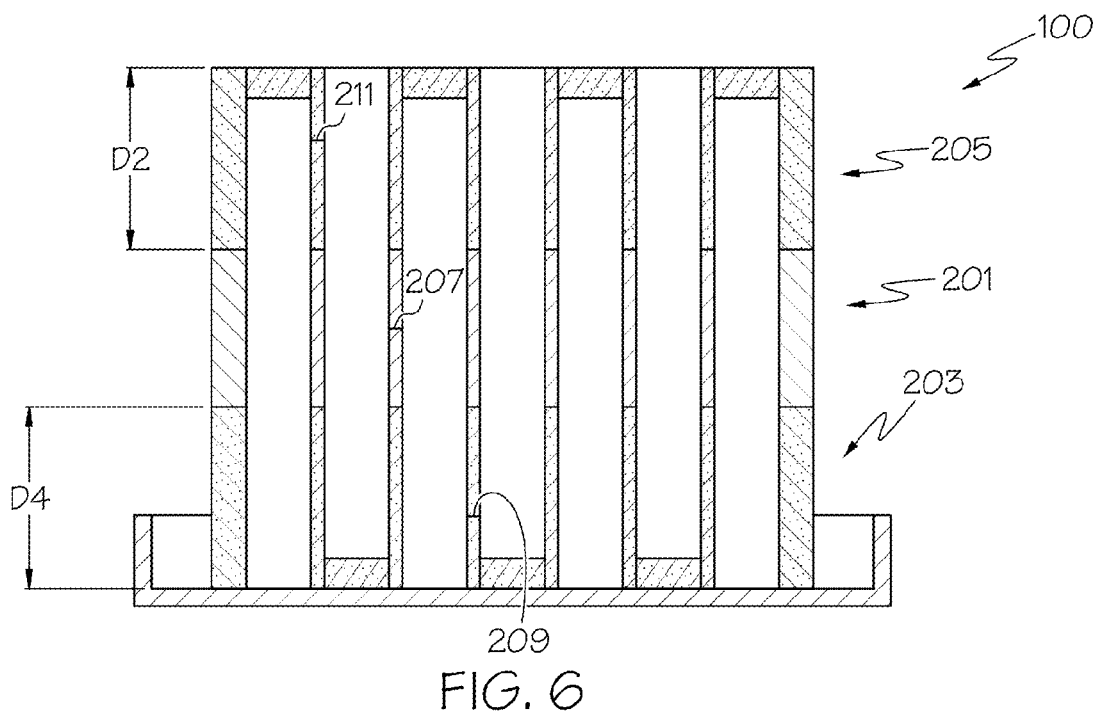
FIG. 6 is a cross sectional view of the honeycomb filter of FIG. 1 after wetting the first end portion of the honeycomb filter.

In one example, the method can include wetting the at least one of the first end portion 203 and the second end portion 205. For example, the first end portion may be wetted to provide at least the first end portion as a wetted end portion. In another example, the second end portion may be wetted to provide at least the second end portion as a wetted end portion. In still further examples both the first end portion and the second end portion may be wetted to provide a first wetted end portion and a second wetted end portion. For example, as shown in FIGS. 3 and 4, the second end portion 205 may be wetted from an initial depth "D1" to a final wetted depth "D2". As shown in FIGS. 5 and 6, the first end portion 203 may likewise be wetted from an initial depth "D3" to a final wetted depth "D4".

The initial and final wetted depths may be similar or identical to one another in some examples. For example, the final wetted depth "D2" of the second end portion 205 may be similar or identical to the final wetted depth "D4" of the first end portion 203. In alternative examples, the initial and/or final wetted depths of the first and second end portions may be different from one another. For example, the final wetted depth "D4" of the first end portion 203 may be substantially different from the final wetted depth "D2" of the second end portion 205.

In some examples, the first end portion and/or the second end portion can be wetted to a depth of at least about 5% of the length of the honeycomb filter. For example, the first end portion and/or the second end portion can be wetted to a depth of at least about 20% of the length of the honeycomb filter. In further examples, the first end portion and/or the second end portion can be wetted to a depth of at least about 30% of the length of the honeycomb filter. In still further examples, the first end portion and/or the second end portion can be wetted to a depth of at least about 40% of the length of the honeycomb filter. Increasing the depth of the wetted end portion can help further reveal otherwise difficult to determine defects in the intermediate portion of the honeycomb filter. By way of example, FIG. 4 illustrates the defect 211 of the second end portion 205 is positioned within the wetted second end portion within the depth D2 while the defect 207 within the intermediate portion 201 remains in an unwetted intermediate portion of the honeycomb filter 100. Furthermore, FIG. 6 illustrates the defect 209 in the first end portion 203 positioned within the wetted first end portion within the depth D4 while the defect 207 within the intermediate portion 201 still remains within the unwetted intermediate portion of the honeycomb filter 100. As such, testing procedures may be carried out, as discussed below, that will enhance the visibility of the defect 207 since the wetting the end portions of the honeycomb filter can act to increase the pressure differential within the intermediate portion 201 during the testing procedure.

Various alternative techniques may be used to wet the first end portion and/or second end portion of the honeycomb filter. For example, wetting may be achieve by exposing the end portion to vapor, dipping the end portion in liquid, soaking the end portion in liquid or other wetting techniques. Vapor or liquid can comprise water vapor or liquid water (e.g., purified water). In other examples the vapor and/or liquid can comprise glycerin, alcohol or other vapor or liquid that will not erode, corrupt or otherwise damage the honeycomb filter. In further examples, wax or other coatings may be used to substantially block air through the end portions, thereby even further increasing the pressure differential within the intermediate portion where substantially all of the fog will be forced to pass. However, such coatings (e.g., wax) may be difficult to remove and may also completely block defects within the end portions, thereby preventing simultaneous identification of defects within the end portions as well as the intermediate portion. Rather, wetting with vapor and/or liquid comprising glycerin, alcohol, water (e.g., purified water), etc. can be easily removed (e.g., by evaporation) and may block passage of the fog through the porous walls while still permitting passage of fog through any defects within the end portions. As such, simultaneous detection of defects within the end portions as well as the intermediate portion can be achieved.

Example techniques for wetting the second end portion 205 will now be described with the understanding that such techniques may be equally carried out for wetting the first end portion 203. Moreover, while the method of wetting the second end portion 205 shown in FIGS. 3-4 is illustrated as being identical to the method of wetting the first end portion 203 shown in FIGS. 5-6, in further examples, different wetting techniques may be applied to achieve the corresponding wetted end portion in further examples.

Soaking techniques will be initially described with reference to wetting the second end portion 205 with the understanding that similar soaking techniques may be carried out to wet the first end portion 203. For example, as shown in FIG. 2, a container 210 such as the illustrated dish may be filled with a quantity of liquid 213 to an initial level "L1". The liquid can comprise water (e.g., purified water) although other liquids (e.g., glycerin, alcohol, etc.) may be used in further examples. The second end portion 205 can then be soaked in the quantity of liquid to provide the second end portion as a wetted end portion. During an example soaking procedure, the second end portion 205 may be submerged within a quantity of the liquid 213, wherein the liquid 213 may then be drawn up by capillary forces to a depth against the force of gravity. As shown in FIG. 4, the liquid may be effectively drawn up by the capillary forces to a final wetted depth "D2" from the second end face 104.

As mentioned previously, example methods may carry out wetting of the first and/or second end portion to a final wetted depth that is within a predetermined range of acceptable depths. Indeed, in some examples, wetting can be carried out to a depth of at least about 5%, such as at least about 20%, such as at least about 30%, such as at least about 40% of the length of the honeycomb filter. In some examples the predetermined range can be from about 5% to about 10%, such as from about 10% to about 20%, such as from about 20% to about 30%, such as from about 30% to about 40% of the length of the honeycomb filter.

Various soaking techniques may be carried out to achieve the desired final wetted depth. For example, as shown in FIG. 2, the quantity of liquid 213 in the container 210 may be predetermined such that the step of soaking draws the entire predetermined quantity of liquid into the wetted end portion. The quantity of liquid can be preselected to achieve the desired final wetted depth "D2". For example, the quantity of liquid may be determined based on prior soaking procedures to determine the extent that the liquid is drawn by capillary action into the end portion of the honeycomb filter. In one particular example, the predetermined quantity of liquid may be calculated to achieve wetting of the second end portion to a predetermined final wetted depth "D2". In an alternative procedure, the second end portion may be soaked a predetermined period of time that is known or calculated to result in the desired final wetted depth "D2".

The final wetted depth may also be obtained by dipping of the end portion within a quantity of liquid. For example, the second end portion 205 may be dipped briefly in a quantity of liquid 213 to a depth approximating the final wetted depth "D2". The honeycomb filter 100 may then be removed from the vicinity of the container 210 wherein excess liquid clinging to the dipped surfaces of the honeycomb filter 100 may be absorbed into the walls to achieve the final wetted depth "D2".

FIG. 6 demonstrates an example where both the first end portion 203 and the second end portion 205 are each wetted to corresponding final wetted depths D4 and D2, thereby leaving an unwetted intermediate portion 201. As mentioned previously, the wetted first end portion 203 helps reduce air flow through the wetted porous walls while still permitting fog to flow through any defect 209 in the first end portion 203. Likewise, the wetted second end portion 205 helps reduce air flow through the wetted porous walls while still permitting fog to flow through any defect 211 in the second end portion 205. As such, the pressure differential within the intermediate portion 201 is increased to help identify any of the defects 207 within the unwetted intermediate portion 201.

The method can further include the steps of flowing a fog with moisture droplets into the honeycomb network of channels at the first end portion of the honeycomb filter and then monitoring the second end portion of the honeycomb filter for moisture droplets of the fog exiting the honeycomb network of channels. The step of flowing the fog and monitoring the second end portion can be carried out in a variety of ways, for example, with a testing apparatus.

Figure 7:
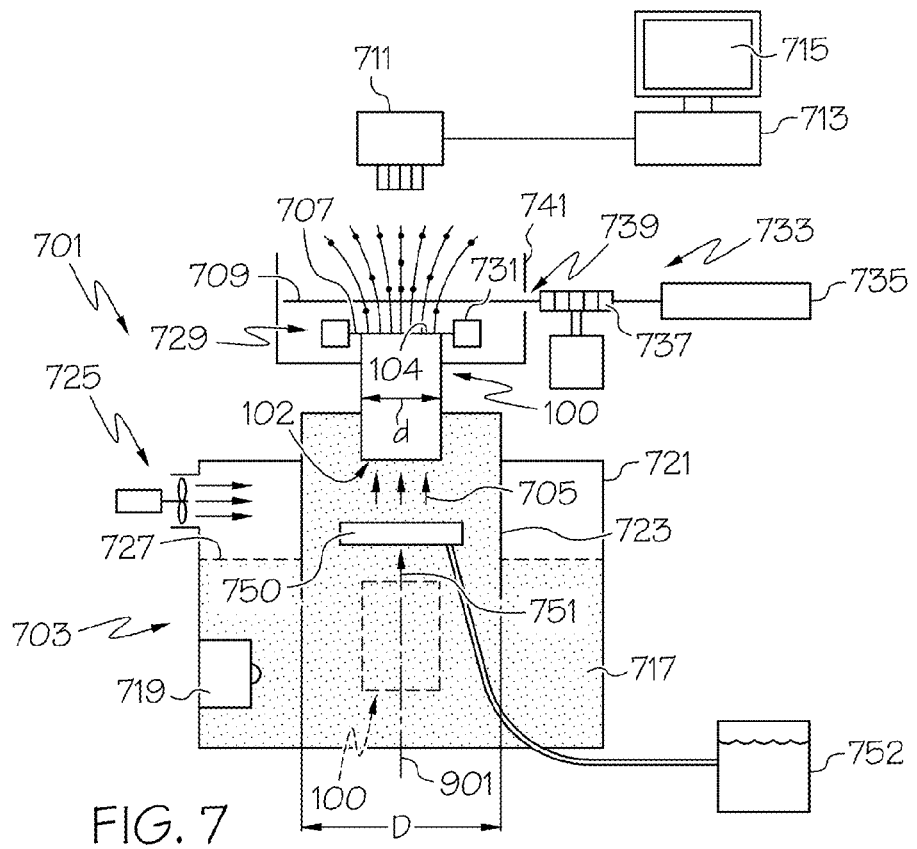
FIG. 7 is a test apparatus being used to test the honeycomb filter of FIG. 6 having wetted first and second end portions.

Various testing apparatus may be provided in accordance with aspects of the disclosure. For example, FIG. 7 illustrates just one example of a test apparatus 701 being used to test the honeycomb filter 100 with wetted ends shown in FIG. 6. The test apparatus 701 is designed to detect defects in the interconnecting porous walls 106 and/or the plugs 112 at one end of the each of the channels 108, 110. As mentioned previously, such defects are desirable to locate and address since they may otherwise affect the performance of the honeycomb filter 100. For example, the porous walls 106 may include defects, such as cracks or holes, that allow relatively unrestricted flow between adjacent cells, thereby short circuiting the filtering process of the porous walls and thereby adversely affecting filtration efficiency and/or filtration integrity. Still further, defects may occur in the plugs 112 as holes or cracks within the plug and/or between the plug and the porous walls 106. In addition, plug defects may result from missing plugs or plugs that only partially fill the end of the channel. As such, the example test apparatus 701 may be provided to allow defects in the honeycomb filter 100 to be readily detected.

As shown, the tests apparatus 701 can include a particulate source 703 which operates to supply a flow of fog (as indicated by arrows "705") which comprises gas with particulates suspended therein. The fog is provided to an inlet end face 102 of the honeycomb filter 100. The particulates of the fog flow pass into the inlet cell channels 108 and through the porous walls 106 and/or plugs 112 of the honeycomb filter 100 and, if not trapped by the porous walls, portions of the fog may exit out through the outlet end face 104. Immediately upon exiting the outlet end face 104, the fog can pass through a permeable member 707, such as a screen mounted adjacent to, and preferably engaged in direct contact with, the outlet end face 104. After exiting the permeable member 707, the particulates of the fog may be illuminated by a plane of light 709 projected in the vicinity of the permeable member 707. In one example, the plane of light 709 may be parallel to a plane of the permeable member 707 and spaced a slight distance above. Defects in the plugs 112 and/or porous walls 106 may then be reliably detected in the honeycomb filter 100 by inspection of the interference between the particulates and the plane of light 709.

In one example, an image indicative of the locations of defective cells is generated, for example by recording an image with an imager 711, such as a camera. The image corresponding to the defective cell locations may be stored in memory in a computer 713 and/or may also be displayed on a video monitor 715. Defects in the porous walls 106 and/or plugs 112 show themselves as bright spots in the image above the honeycomb filter 100, i.e., at the intersection with the plane of light 709. Accordingly, their location may be easily correlated with a cell defect location on the honeycomb filter 100. In particular, before laying the permeable member 707 on top of the honeycomb filter 100, a previous image may be recorded of the outlet end face 104, thereby capturing an image of the honeycomb cell structure, i.e., the location in coordinate space (along the plane of the outlet end face 104) of the peripheral outline and the respective locations of the cells and plugs on the outlet end face 104. This image may then be correlated with the other image illustrating the bright spots to assign various cells as including defects.

The particulates can comprise liquid particles, such as fine liquid particles. In operation, the particulates may be formed in a chamber 717 by a particle generator 719 of the particulate source 703. The particulates may be generated by nebulizing, atomizing or otherwise spraying liquid through a nozzle. As mentioned previously, the liquid may be water (e.g., purified water), a water-based solution, and/or a glycol-based solution that is provided at a fog. While water or other liquid may be used, in alternative examples, smoke or other fine suspended particulate matter may be used in accordance with aspects of the disclosure. The particulates may be housed in a housing 721 and provided under pressure through a flow path, which may be optionally defined by a pipe 723 positioned between the particulate source 703 and the inlet end face 102 of the honeycomb filter 100. The pipe 723, if provided, may include an optional round cross-section although other cross-sectional shapes are possible such as triangular, rectangular (e.g., square), or other polygonal shape or may comprise an elliptical or other curvilinear shape. In one example, the pipe 723, if provided may be axially aligned with the honeycomb filter 100. Further, preferably the inner dimension, D, (e.g., diameter) of the pipe 723 at the point where the particulate laden gas is provided to the inlet end face 102 (near the pipe's upper end) is larger than a maximum transverse outer dimension, d, of the honeycomb filter 100. This feature improves the uniformity of the flow velocity profile, by reducing the effect of boundary layer flow on the flow distribution of the gas, provided across the inlet end face 102. The provision of pressure, preferably at greater than 30 Pa (relative pressure between the inlet and ambient), is achieved by a fan 725 forcing air into the housing 721. In some embodiments, the pressure is between 30 and 70 Pa. A perforated partition 727 may be employed to minimize variations in pressure within the chamber 717.

Upon passing through the honeycomb filter 100, the particulates contained in the gas flow pass through the permeable member 707. The permeable member 707 may be a screen, mesh, cloth, or perforated sheet. In one example, the permeable member 707 may be manufactured from a filamentary material, such as a woven or interlaced strand or wire material having multiple oriented strands. The strands may be oriented in a generally perpendicular manner; although this orientation is not required. For example, the member may be woven in chain link orientation. In one example, wire cloth or mesh may be provided. In another example, metal wire cloth, such as stainless steel wire cloth, may also be used. The permeable member 707 preferably includes a mesh density of greater than about 50 threads/inch, or even greater than 125 threads/inch, and in some embodiments greater than about 250 threads/inch. The diameter of the wire strands (filaments) in the mesh or cloth may be less than about 0.005 inch (less than about 127 microns), less than about 0.004 inch (less than about 102 microns), or even less than about 0.002 inch (less than about 51 microns). In one exemplary embodiment, the permeable member 707 includes wire mesh density of greater than about 50 threads/inch, and a diameter of the wire is preferably less than about 0.004 inch (less than about 102 microns). A fine screen having a 30 micron diameter and 325 threads/inch may be provided. Permeable member 707 may also be chiffon or other knit cloth or mesh, or any other finely knitted, interlaced, or grid forming cloth material.

The permeable member 707 may be disposed adjacent to or in contact with the outlet end face 104 of the honeycomb filter 100. As shown, an image enhancement apparatus 729 may be provided with a frame 731 (e.g., an annular frame) configured to mount the permeable member 707 within a central area defined by the frame 731. In one example, the permeable member 707 may be stretched across the frame 731 so as to construct a plane, and preferably held by the frame, such as an adjustable diameter ring frame.

In some examples, the permeable member 707 may include an anti-reflective surface. If provided, the anti-reflective surface may be substantially absorbing of the light of the wavelength of the light source used for illumination. For example, the screen may be colored with a dark surface coloring, for example flat black or matte black or other colors that are absorbing, such as brown or navy blue. Embodiments may include a coating, such as a black oxide coating. The dark coloring helps improve the signal-to-noise level between the signal and lower the background noise.

In one example, an illumination apparatus 733 is provided with a light source 735 for generating the plane of light 709 adjacent to and spaced from the outlet end face 104 of the honeycomb filter 100. The plane of light 709 may also be spaced from the plane of the permeable member 707. One example of a light source 735 is configured to generate the plane of light 709 as a red or green laser although other laser types or light devices may be used in further examples. The light source 735 may be configured to cooperate with optical elements, such as a rotating faceted mirror 737, to convert the light beam to the planar sheet of light 709. The illumination apparatus 733 is configured to produce the plane of light 709 that may be generally parallel to the outlet end face 104 and a plane of the permeable member 707. The plane of light 709 can also be large enough to fully span across the end face 104 of the honeycomb filter 100.

In further examples, it may be desirable to control the spread of the plane of light 709. In such examples, a slot 739 may be formed in uprights 741 through which the plane of light 709 extends such that a well-defined plane of light 709 is projected above the outlet end face 104. The width of the slot 739 defined by the upright 741 can be selected to control spread of the plane of light 709. The uprights 741 can also control eddy current and otherwise minimize air flow disturbances around the honeycomb filter 100. Preferably, the distance between the plane of light 709 and the outlet end face 104 is such that the particulates emerging from the outlet end face 104 still have sufficient momentum to intersect the plane of light 709. Thus, plane of light 709 may be designed to be as close as possible to the outlet end face 104 and permeable member 707 without interfering with the outlet end face 104. In one embodiment, the distance between the plane of light 709 and the permeable member 707 is in a range from $\frac{1}{16}$ in. (1.6 mm) to $\frac{1}{2}$ in. (12.7 mm).

In further examples, other light sources may be provided such as ultraviolet light or infrared lasers to produce the plane of light.

After particulates emerge from the permeable member 707, the illumination apparatus 733 is configured to illuminate the particulates in the flow and an imager 711 may be configured to capture an image of the X-Y position of particles illuminated (the bright spots) due to interference with the plane of light 709 as the particles emerge from the outlet end face 104 of the honeycomb filter 100. The imager 711 may record an image (e.g., digital image), of the interference pattern of the flow emerging from the permeable member 707. The image may then be processed to detect the presence of, and location of, defective cells/plugs, such that corrective action (e.g., repairing, discarding, etc.) may be taken. Image processing may include a pixel-by-pixel comparison of the image against an intensity threshold. The process methodology may indicate a defect when the intensity is above a pre-selected threshold.

The imager 711, such as a camera or camcorder, may be positioned above the outlet end face 104 of the honeycomb filter 100 to capture an image of any illuminated particles flowing out of the outlet end face 104. In particular, the areas where defects are indicated show up as bright spots in the image. In the case of a single defect, the defect is identified as a relatively bright spot located above the cell that has particulate within the gas stream due to the defect within the honeycomb filter 100. As such, an analysis of the image can help immediately locate the X-Y position of the defect along the outlet end face 104. The imager 711 may further include an optical system, such as lenses, for focusing on the illuminated region. The imager 711 may include or be attached to an internal processor or computer 713 which processes information collected by the imager into image files and stores the image files in memory. The processor may support various types of image file formats, such as TIFF and JPEG or other file formats. The computer 713 may include a video monitor 715 and other peripheral devices necessary for interacting with the system, such as a keyboard and mouse (not shown). The image files from the imager 711 can be transferred to the computer 713 further processing. The image files may also be displayed on the video monitor 715.

Cells in the honeycomb filter 100 having defects would discharge more particulates and larger particulates than cells not having defects. The size of the spots can provide an indication of the size of the defects in the honeycomb filter 100. If the image appears uniform, then the test would indicate no defects in the honeycomb filter 100. Advantageously, the use of the permeable member 707 can reduce the overall background objects that may confuse the image, thereby increasing the signal-to-noise ratio such that the bright spots associated with defects may be more readily detected.

Example methods of testing a honeycomb filter 100 will now be described. Initially, as shown in FIG. 1, the honeycomb filter 100 may be provided with the intermediate portion 201 disposed between the first end portion 203 and the second end portion 205 along the length "L" of the honeycomb filter 100. The honeycomb filter 100 includes the honeycomb network of channels 107 defined by the plurality of intersecting porous walls 106. The honeycomb network of channels 107 extend along the length "L" of the honeycomb filter 100 between the first end portion 203 and the second end portion 205. In one example a first end portion and/or a second end portion of the honeycomb filter may be wetted such that the wetted end portion has a higher degree of wetness than the intermediate portion. In one example, the method includes the step of wetting the first end portion 203 to a depth of from about 5% to about 40% of the length "L" of the honeycomb filter 100 to provide a first wetted end portion having a higher degree of wetness than the intermediate portion. In addition or alternatively, in another example, the method includes the step of wetting the second end portion to a depth of from about 5% to about 40% of the length of the honeycomb filter to provide a second wetted end portion having a higher degree of wetness than the intermediate portion. As discussed above, the step of wetting can be carried out with a liquid, such as water although other liquids may be used in further examples. Moreover, as discussed above, the method of wetting can be carried out by exposing the ends to vapor, dipping in a quantity of water, soaking in water and/or other wetting techniques.

Figure 8:
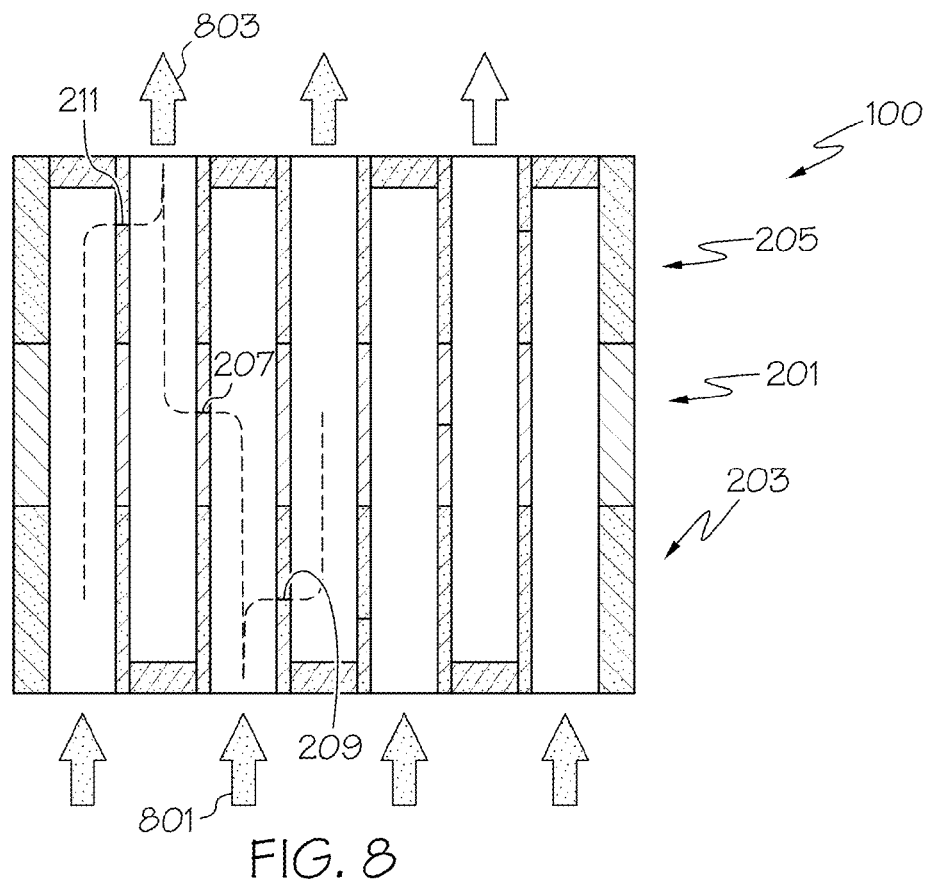
FIG. 8 illustrates fog flow through the honeycomb filter of FIG. 6 when testing using the test apparatus of FIG. 7.

As shown in FIG. 8, the wetted end portions 203 and 205 can help plug corresponding pores within the porous walls of the end portions while still permitting flow of fog through defects 209, 211 located within the corresponding end portions 203 and 205. At the same time, the pressure differential is increased within the intermediate portion 201, thereby allowing increased flow of fog through the defect 207 within the intermediate portion 201. As such, analysis of any defects located within the intermediate portion 201 may be carried out in a more effective manner.

The method can include flowing a fog 801 with moisture droplets into the honeycomb network of channels at the first end portion 203 of the honeycomb filter 100. For example, referring to FIG. 8, the test apparatus may be used to flow fog 801 with moisture droplets into the honeycomb network of channels. Moreover, the method can include the step of monitoring the second end portion 205 of the honeycomb filter for moisture droplets of the fog exiting the honeycomb network of channels. In one example, the test apparatus 701 may be used to monitor the second end portion 205, for example, by illuminating moisture droplets of the fog exiting the honeycomb network of channels.

As such, referring to FIG. 8, wetting of the end portions 203, 205 can at least partially (e.g., completely) plug the pores within the corresponding end portions. As such, increased pressure differential may be achieved within the intermediate portion 201 to allow enhanced detection of any defects 207 within the intermediate portion. At the same time, wetting the end portions may be insufficient to plug the defects 209 and 211 within the corresponding end portions. As such, wetting the end portions can increase the sensitivity of the testing apparatus, thereby allowing enhanced detection of the defects 207 within the intermediate portion while also permitting detection of defects 209, 211 within the end portions.

An experiment was conducted on a honeycomb filter where 9 artificially created defects in the filter were created. Three defects where generated in each of the first end portion, the second end portion and the intermediate portion of the honeycomb filter. A nebulizer test was performed on the dry filter wherein fog was passed through the first end of the filter while the second end of the filter was monitored. The displayed pixel size of each defect was recorded. Then, both ends were wetted and the same nebulizing procedure was carried out wherein the pixel size of each defect was noted again. The test noted that the pixel size of all three defects in each of the first end portion, second end portion and intermediate portion of the honeycomb filter was greater with the honeycomb filter having wetted end portions when compared to the honeycomb filter having dry end portions.

The testing found an increase in detectability of 1.6× of defects within the first end portion, an increase in detectability of 5.8× of defects within the intermediate portion, and an increase in detectability of 1.8× of the defects within the second end portion.

Defects within outer peripheral channels may also be more difficult to detect than defects located within interior channels. As such, in accordance with one aspect of the disclosure, an outer peripheral surface 109 of the honeycomb filter 100 may be wetted to enhance flow of fog through outer peripheral channels of the honeycomb network of channels.

Figure 9:
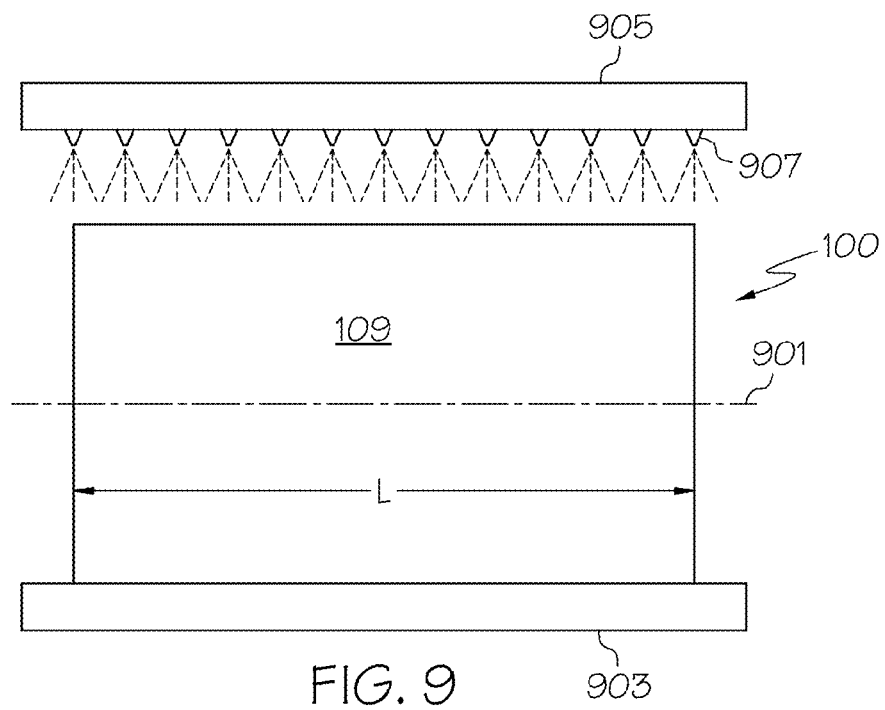
FIG. 9 illustrates a method of wetting an outer peripheral surface of the honeycomb filter.
Figure 10:
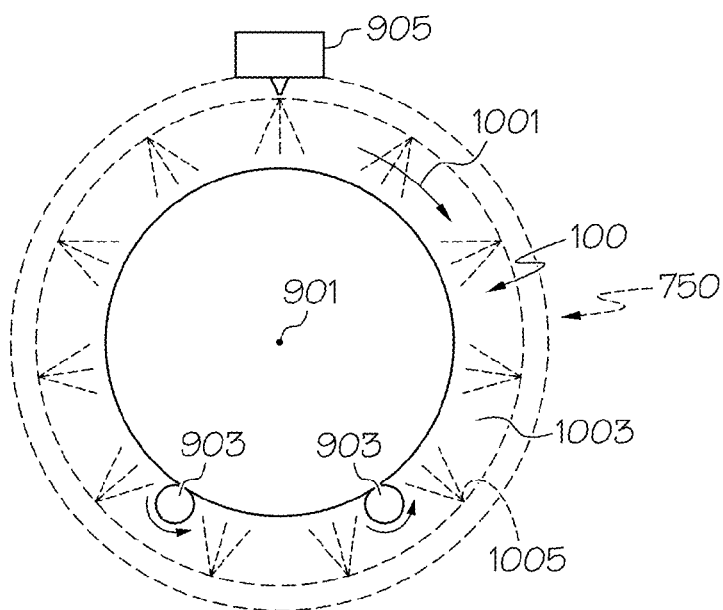
FIG. 10 is a side view of the method of wetting the outer peripheral surface of the honeycomb filter shown in FIG. 9.
Figure 11:
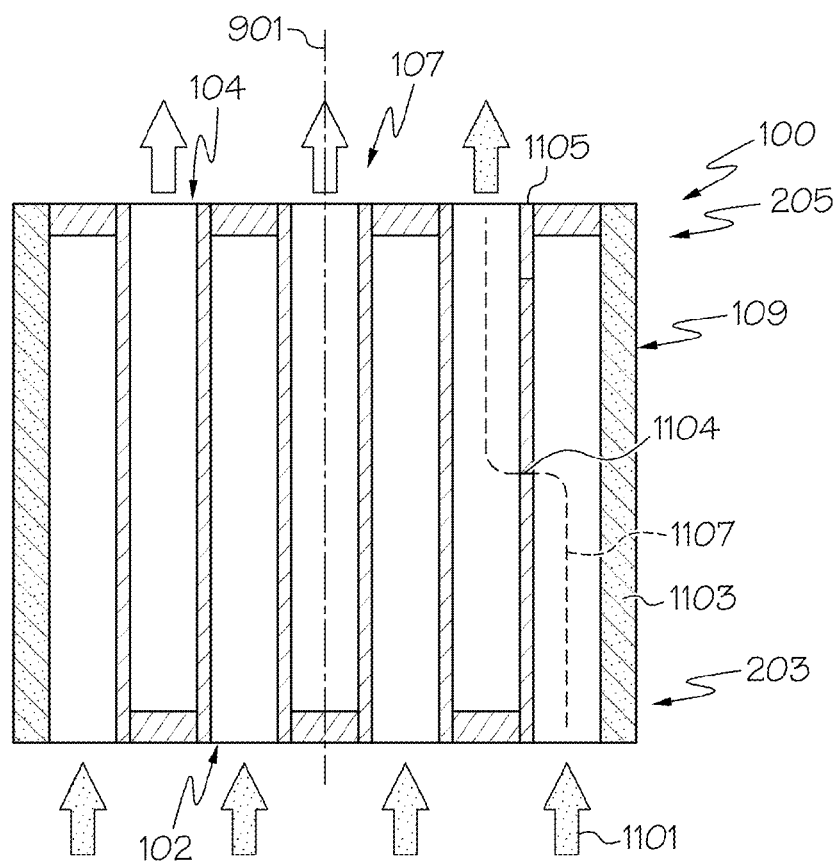
FIG. 11 illustrates fog flow through the honeycomb filter with a wetted outer peripheral surface when testing using the test apparatus of FIG. 7.

FIGS. 9 and 10 illustrate just one example of wetting the outer peripheral surface 109, such as an outer peripheral skin of the honeycomb filter 100. For example, the central axis 901 may be oriented at an angle relative to vertical and can even be located horizontal as shown in FIG. 9. As shown in FIGS. 9 and 10, the one or more rollers 903 may rotate to allow the honeycomb filter 100 to rotate along direction 1001 about the central axis 901. During rotation, a spraying arm 905 may extend along the length "L" of the honeycomb filter 100. As such, as the honeycomb filter 100 rotates about the central axis 901, a series of spray nozzles 907 disposed along the length "L" of the honeycomb filter 100 allow the liquid to coat the outside of the outer peripheral surface 109. The liquid, such as water (e.g., purified water), a water-based solution, a glycol-based solution or other liquid, may then soak into the outer peripheral surface 109.

FIGS. 7 and 10 illustrate another example of wetting the outer peripheral surface 109. As shown in broken lines in FIG. 7, the honeycomb filter 100 may be oriented with the central axis 901 of the honeycomb filter 100 being substantially vertical. A peripheral spray ring 750 may be provided in communication with a pressured water supply 752. The honeycomb filter may be moved up in a direction 751 of the axis through a central passage of the peripheral spray ring 750. A somewhat schematic illustration of the peripheral spray ring 750 is illustrated in broken lines in FIG. 10 as an alternative to the illustrated spraying arm 905. As shown, the spray ring include a central passage 1003 with a plurality of nozzles 1005 oriented to spray liquid towards an interior of the peripheral spray ring 750. As such, turning back to FIG. 7, the honeycomb filter 100 may be moved upward in direction 751 through the central passage 1003 of the peripheral spray ring as the honeycomb filter 100 is in the process of being mounted in position for testing by the test apparatus 701.

Once the outer peripheral surface 109 is wetted, the outer peripheral surface 109 (e.g., the provided by the illustrated outer peripheral skin) is loaded with liquid. As such, particulate within the fog 1101 is not as likely to be absorbed by the outer peripheral surface 109 since the outer peripheral surface 109 is already loaded with a quantity of liquid. Rather, the particulate within the fog 1101 is more likely to reach the defect 1104 located in an outer peripheral wall 1105 of the network of channels 107. As such, as shown, the particulate path 1107 can eventually leave the outlet end face 104 for detection by the test apparatus 701.

As such, methods of testing a honeycomb filter 100 are provided. The methods include the step of providing the honeycomb filter 100 including the first end portion 203 and the second end portion 205 along the axis 901 of the honeycomb filter 100. The honeycomb filter 100 can include the network of channels 107 defined by the plurality of intersecting walls 106. The honeycomb network of channels 107 extend along the axis 901 of the honeycomb filter 100 between the first end portion 203 and the second end portion 205. The honeycomb filter 100 is provided with an outer peripheral surface 109 circumscribing the honeycomb network of channels 107 and extending between the first end portion 203 and the second end portion 205. As shown, in one example, the honeycomb filter 100 can include an optional outer peripheral skin 1103 that provides the outer peripheral surface 109.

The outer peripheral skin 1103 may be provided in various ways. For example, the outer peripheral skin 1103 may be simultaneously formed with the plurality of intersecting walls 106. For instance, the intersecting walls 106 may be coextruded with the outer peripheral skin 1103 from a batch of ceramic and/or ceramic-forming material. Alternatively, the intersecting walls 106 may be extruded and then the outer peripheral skin 1103 may be subsequently applied. In one example, the intersecting walls 106 are formed. The outer periphery of the intersecting walls 106 may be optionally machined and then the outer peripheral skin may be applied, for example, by way of a doctor blade or other application technique.

Testing can then proceed by wetting the outer peripheral surface 109, for example, spraying techniques described with respect to FIG. 10 above. In one example, the spraying techniques include spraying with a liquid, for example glycerin, alcohol, water (e.g., purified water). For instance, referring to FIG. 7, the honeycomb filter 100 may be loaded into an interior area of the particulate source 703. The method can then translate the honeycomb filter 100 in a direction of the axis of the honeycomb filter through the central passage of a peripheral spray ring 750 while the spray ring wets the outer peripheral surface 109 of the honeycomb filter 100.

Wetting the outer peripheral surface 109, for example, can load the outer peripheral skin 1103 with moisture. Next, the method can proceed by flowing a fog with moisture droplets into the honeycomb network of channels at the first end portion 203 of the honeycomb filter. After being wetted, for example, by the peripheral spray ring 750, the honeycomb filter can be loaded into position as shown in FIG. 7. Then the second end portion 205 of the honeycomb filter can be monitored for moisture droplets of the fog exiting the honeycomb network of channels. As the outer peripheral surface of the honeycomb filter was wetted, fog within the outer peripheral channels will not have the tendency of being absorbed to the extent it would if the outer peripheral skin was tested when initially dry. As such, wetting the outer peripheral surface 109 prior to beginning the procedure of monitoring the fog exiting the second end portion of the honeycomb substrate can enhance the flow of fog through the outer peripheral channels and thereby allow defects associated with the outer peripheral walls of the intersecting walls 106 to be more readily identified.

Figure 12:
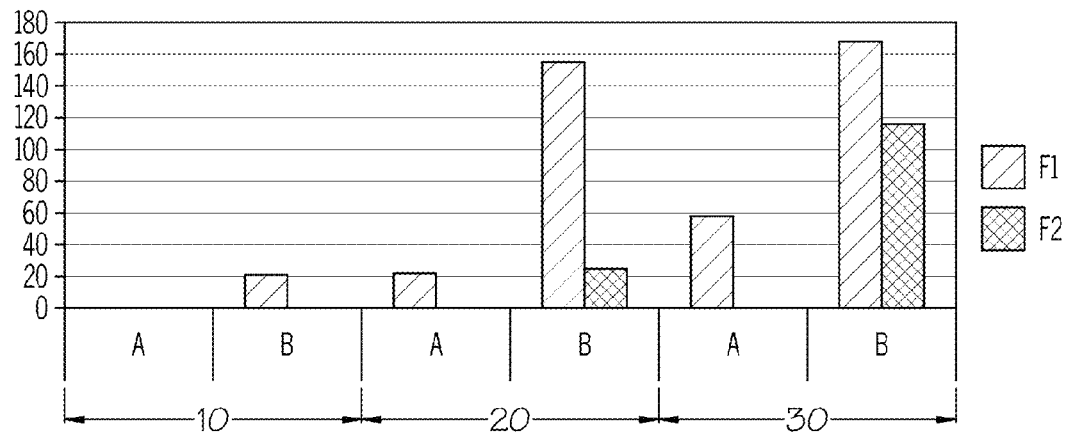
FIG. 12 represents test results illustrating the effectiveness of saturating the outer peripheral skin of the honeycomb filter prior to conducting the testing procedure with the testing apparatus of FIG. 7.
Figure 13:
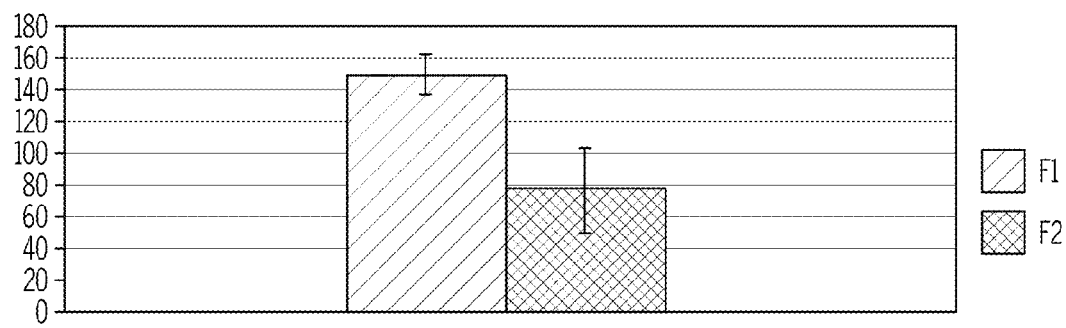
FIG. 13 illustrates repeatability for honeycomb filters with a wetted outer peripheral skin after 30 seconds of testing.

FIGS. 12 and 13 represent test results illustrating the effectiveness of saturating the outer peripheral skin of a honeycomb filter prior to conducting a testing procedure with a nebulizer configuration. Both FIGS. 12 and 13 used a filter with two known flaws (i.e., defects) provided in the perimeter of the part. The two flaws are represented by two different cross-sectional appearances referenced in the legend of the graphs as "F1" (i.e., flaw 1) and "F2" (flaw 2) The vertical axis (i.e., Y-axis) in the graphs are the pixel size of the observed flaw. The regions "A" in the horizontal (i.e., X-axis) of FIG. 12 indicates test results for a dry honeycomb filter while the regions "B" indicate test results for a honeycomb filter wherein the outer peripheral surface was wetted prior to the test procedure. Test results were taken after 10 seconds, 20 seconds and 30 seconds as indicated by "10", "20", and "30" along the horizontal (i.e., X-axis) of FIG. 12.

Referring to region "A" of FIG. 12 after 10 seconds of testing, neither of the flaws "F1" or "F2" the dry honeycomb filter was identified. Referring to region "B" of FIG. 12 after 10 seconds of testing, the first flaw "F1" was identified but the second flaw "F2" was not yet identified.

Referring to region "A" of FIG. 12 after 20 seconds of testing, only the first flaw "F1" of the dry honeycomb filter was identified. However, as indicated by region "B" after 20 seconds of testing, both flaws "F1" and "F2" were identified and the pixel size associated with the first flaw "F1" was significantly larger than the pixel size of the same flaw after 10 seconds.

Referring to region "A" of FIG. 12 after 30 seconds of testing, only the first flaw "F1" of the dry honeycomb filter was identified (although more pronounced) while the second flaw "F2" was not identified. In contrast, as indicated by region "B" after 30 seconds of testing, both flaws "F1" and "F2" were again identified and the pixel size associated with both flaws were again greater than the corresponding pixel size of the flaws after 20 seconds of testing.

As such, without wetting the outer peripheral skin of the honeycomb filter, the second flaw "F2" would never have been detected. In contrast, wetting the outer peripheral surface resulted in detection of more flaws that were more visible when compared to dry honeycomb filters. As shown, increased time of testing can result in greater chance of detection and more visible flaws. In some examples of the disclosure, testing can include wetting the outer peripheral skin of the honeycomb filter and then testing for flaws with a nebulizer or other fog generator for greater than or equal to 10 seconds, for example greater than or equal to 20 seconds, for example greater than or equal to 30 seconds, for example greater than or equal to 40 seconds.

FIG. 13 illustrates the repeatability (displayed by the error bars) for honeycomb filters with a wetted outer peripheral skin after 30 seconds. The sample size was five runs and one standard deviation is shown by the error bars. As indicated, wetting the outer peripheral skin prior to testing was effective in detecting both flaws "F1" and "F2" at a pixel size of greater than 45.

In addition or in alternative to wetting the outer peripheral surface 109, a flow of fog through inner peripheral channels may be inhibited, such as prevented, to enhance the flow of fog through the outer peripheral channels. For example, the method can include the step of obstructing a flow of fog through the inner peripheral channels at the first end portion 203 of the honeycomb filter 100. In addition or in the alternative, the method can include the step of obstructing a flow of fog through the inner peripheral channels at the second end portion 205 of the honeycomb filter 100.

Figure 14:
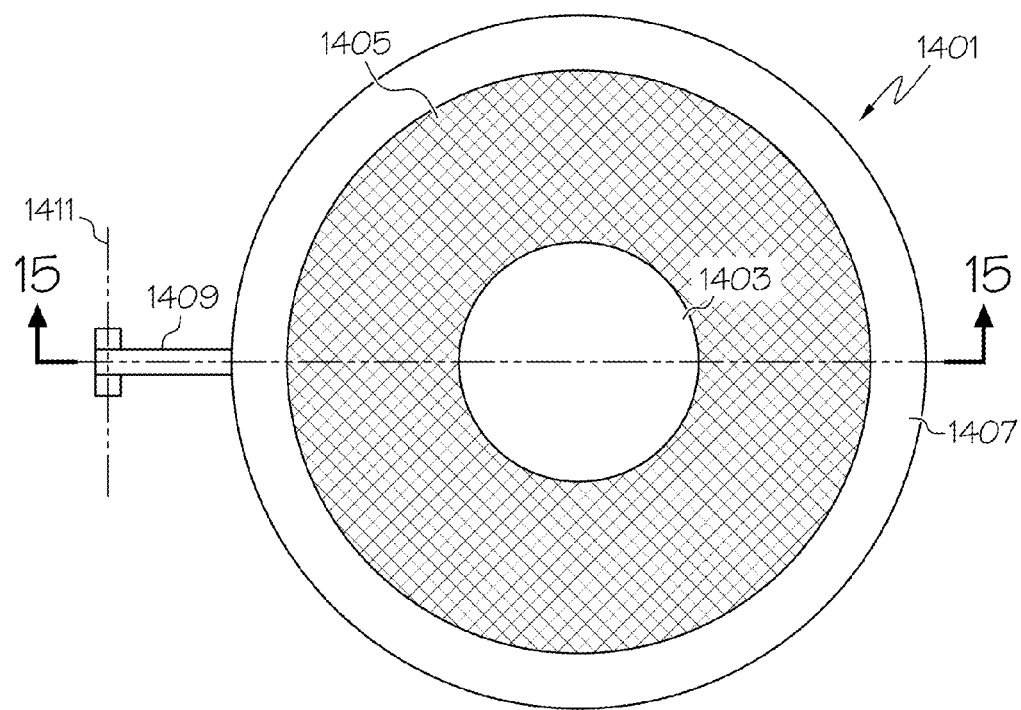
FIG. 14 illustrates a blocking apparatus configured to reduce, such as prevent, the flow of fog through inner peripheral channels of the honeycomb filter when conducting a testing procedure with the testing apparatus of FIG. 7.
Figure 15:
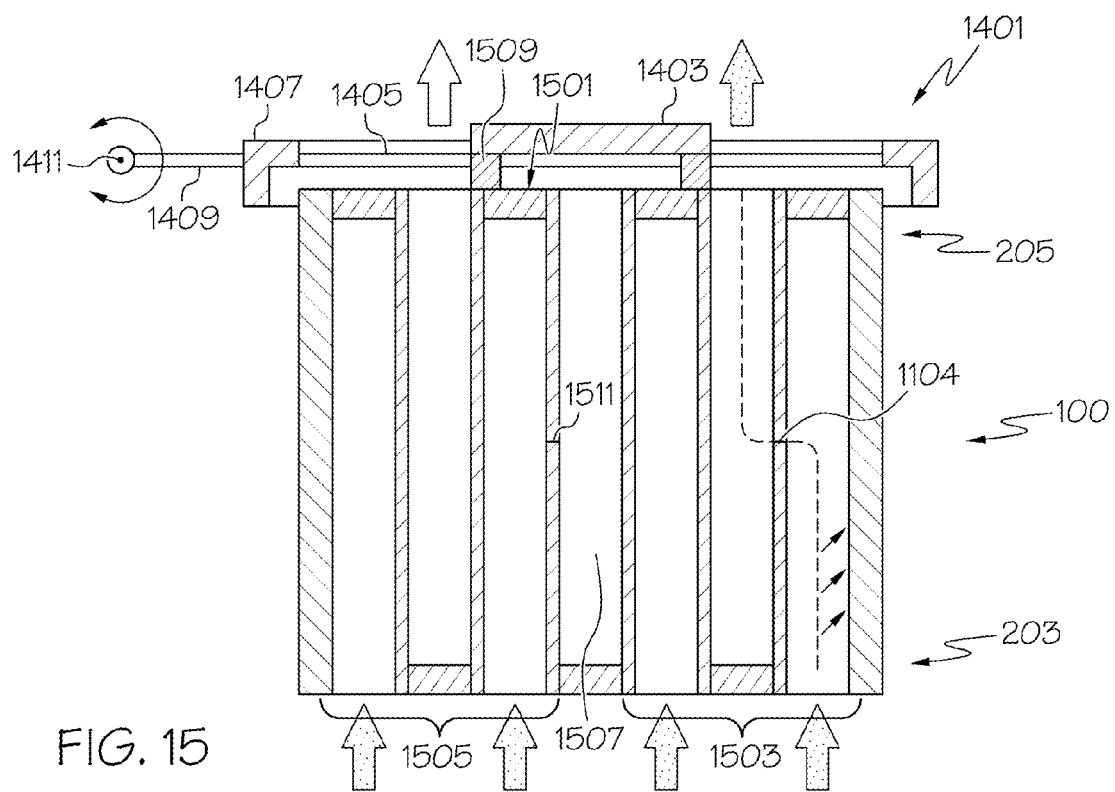
FIG. 15 is a sectional view of the blocking apparatus in a closed orientation wherein a blocking member engages a central portion of the second end portion of the honeycomb filter along line 15-15 of FIG. 14.
Figure 16:
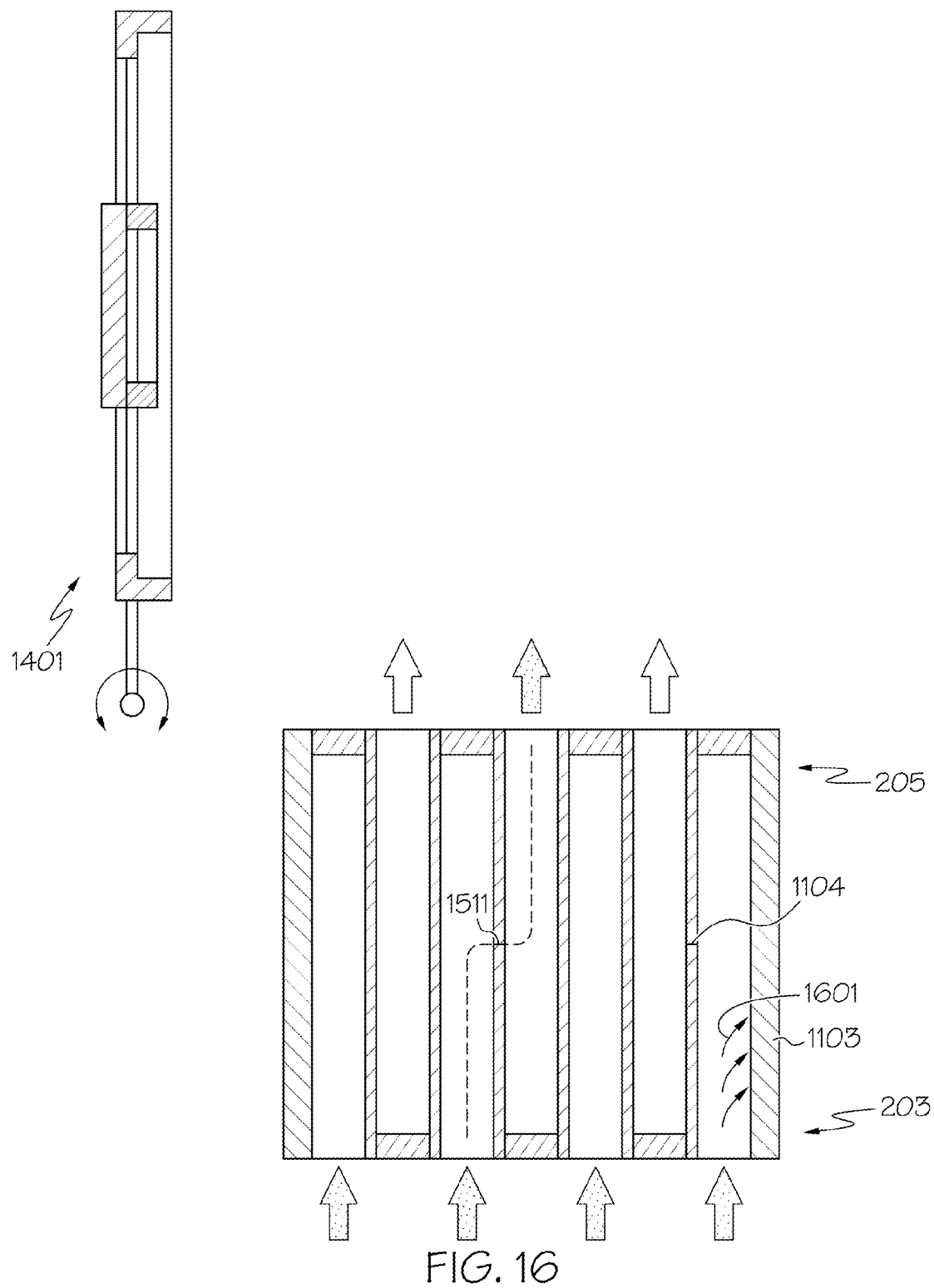
FIG. 16 illustrates the blocking apparatus of FIG. 15 being pivoted to an open orientation.

FIGS. 14-16 illustrate apparatus and methods of testing by obstructing a flow of fog through the inner peripheral channels at the second end portion 205. In one example, the apparatus for testing the honeycomb filter can comprise a flow diverter configured to enhance the flow of fog through the outer peripheral channels 1503, 1505 while reducing, for example preventing, the flow of fog through the inner peripheral channels 1507.

In one example, the flow diverter can substantially completely prevent the flow of fog through the inner peripheral channels 1507. FIGS. 14-15 illustrate just one example of a blocking apparatus 1401 that may be provided with a blocking member 1403 configured to engage a central portion 1501 of the second end portion 205 of the honeycomb filter 100 to enhance the flow of fog from the fog generator through the outer peripheral channels 1503. The blocking member 1403 can comprise a plate constructed of plastic, metal or other material configuration substantially impermeable to gas flow. As shown in FIG. 15, in just one example, the blocking member 1403 can include a peripheral seal 1509 configured to seal against the honeycomb filter 100. As further illustrated, the apparatus may also include a support mesh 1405 supporting the blocking member 1403 within a central portion of the support mesh 1405. For example, a peripheral frame 1407 may be provided to help mount the support mesh 1405, for example, in a substantially planar orientation. As shown in FIG. 15, the blocking member 1403 may be mounted to one side of the support mesh 1405 while the peripheral seal 1509 is mounted to the other side of the blocking member 1403. The support mesh 1405 is gas permeable to allow free movement of fog or gas associated with the fog to pass through the support mesh and thereby freely exit the second end portion 205 of the honeycomb filter 100. At the same time, the gas permeable mesh still provides sufficient support to allow sufficient engagement of the peripheral seal 1509 to inhibit, such as prevent, movement of gas through the inner peripheral channels 1507.

In further examples, the blocking member 1403 is configured to pivot between a blocking orientation (see FIG. 15) and a retracted orientation (see FIG. 16). For example, as shown in FIGS. 14 and 15, the apparatus can include a pivot arm 1409 configured to pivot about a pivot axis 1411 between the closed orientation and the open orientation. As shown, in FIG. 14, in the closed orientation, the flow of fog through the inner peripheral channels 1507 is obstructed to enhance the flow of fog through the outer peripheral channels 1503, 1505. As such, a defect 1104 in the outer peripheral channel is more likely to be detected at the second end portion 205, for example, by the test apparatus 701 shown in FIG. 7. However, as the flow of fog is blocked through the inner peripheral channels 1507, inner defects 1511 associated with the inner channels cannot be detected by the test apparatus 701.

To detect the inner defects 1511, the blocking member 1403 can also be pivoted to an open orientation, as shown in FIG. 16, wherein fog is free to flow in all of the channels. As shown by arrows 1601, fog may be absorbed by the dry outer peripheral skin 1103 prior to reaching the defect 1104. As such, fog may not short circuit through the defect 1104 in sufficient quantities to be detected at the second end portion. However, as the central channels are not adjacent the outer peripheral skin 1103, absorption issues are not a concern. As such, as shown in FIG. 16, the fog entering the first end portion 203 may pass through the defect 1511 to allow the defect to be observed by the test apparatus 701 at the second end portion of the honeycomb filter 100.

As such, the test apparatus 701 can include a blocking apparatus 1401 that allows monitoring for defects associated with the inner peripheral channels 1507 when the blocking apparatus is oriented in the open orientation (see FIG. 16). The blocking apparatus 1401 can also allow for monitoring of defects associated with the outer peripheral channels 1505, 1507 when the blocking apparatus 1401 is oriented in the closed orientation shown in FIG. 15.

Figure 17:
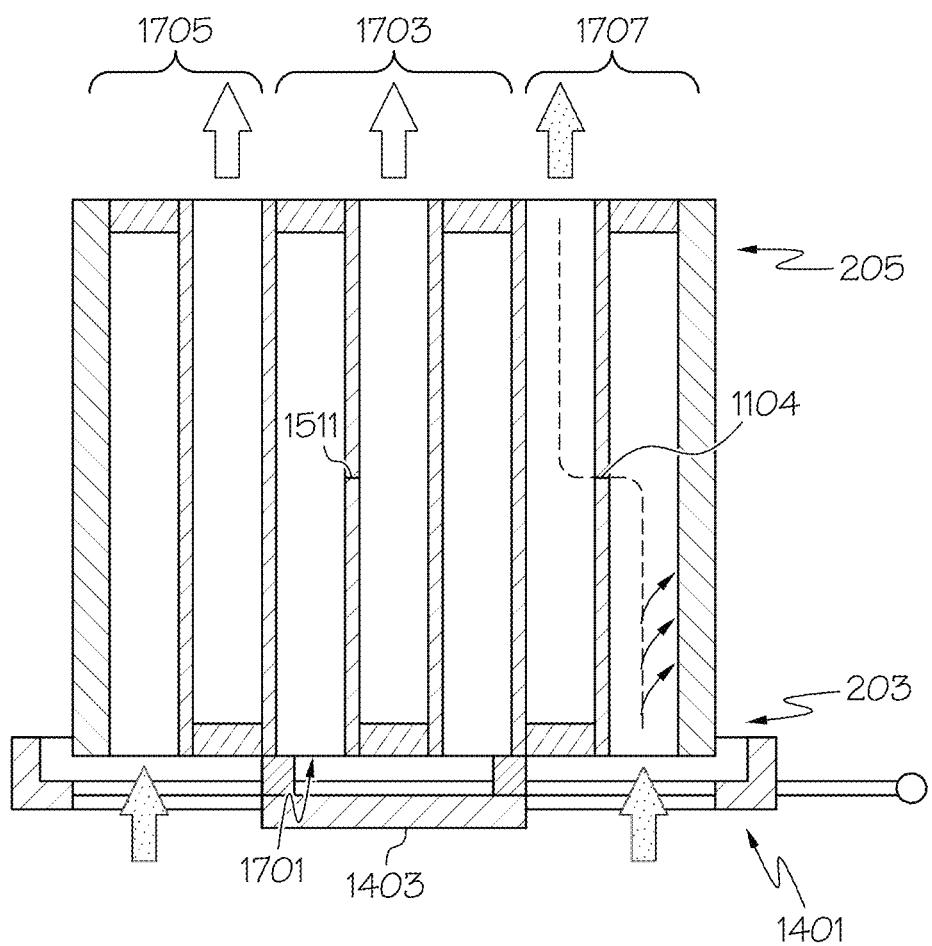
FIG. 17 a sectional view of the blocking apparatus in a closed orientation wherein a blocking member engages a central portion of the first end portion of the honeycomb filter.
Figure 18:
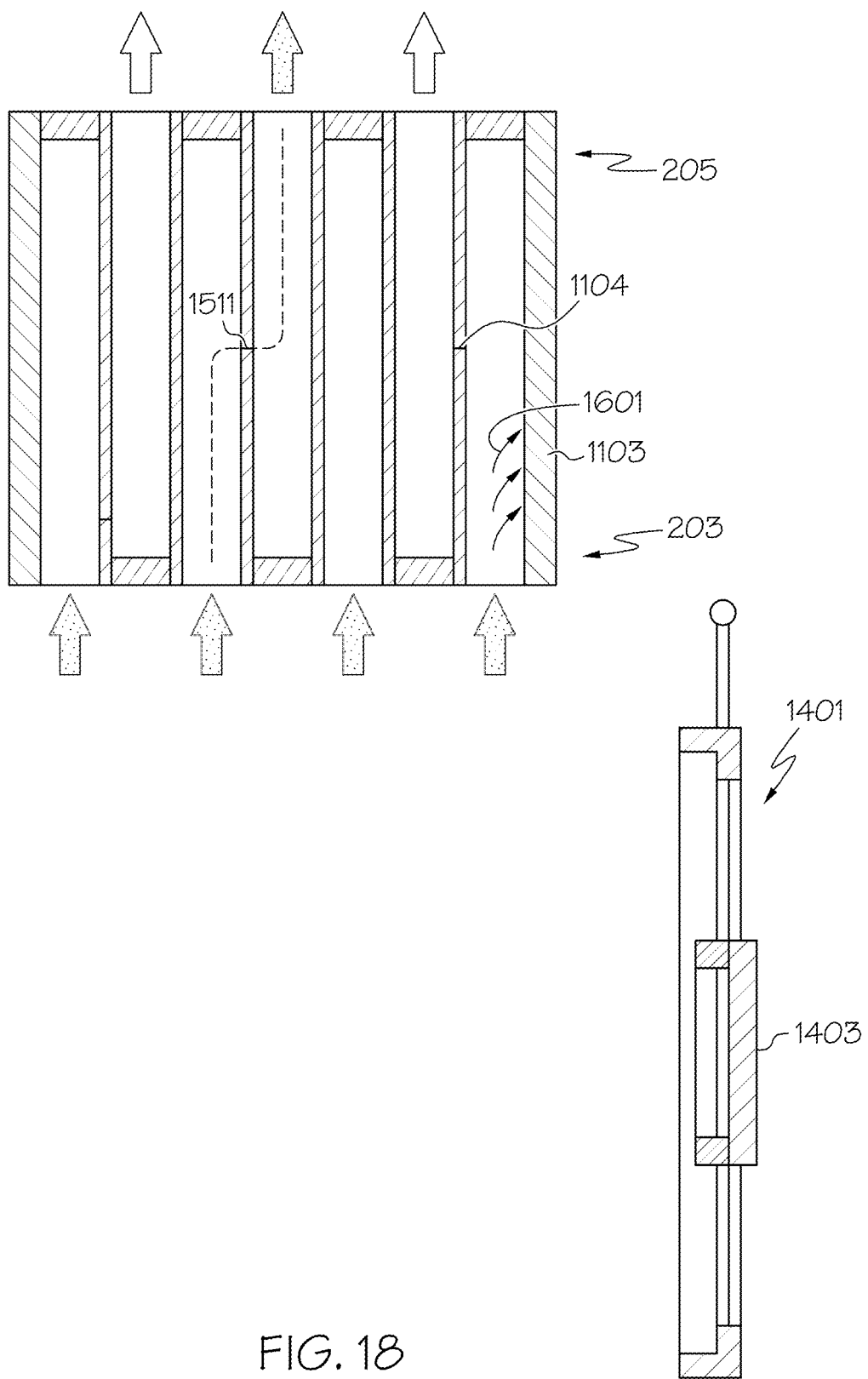
FIG. 18 illustrates the blocking apparatus of FIG. 17 being pivoted to an open orientation.

FIGS. 17-18 illustrate another example wherein the previously-described blocking apparatus 1401 that may be provided with the blocking member 1403 configured to engage a central portion 1701 of the first end portion 203 of the honeycomb filter 100 to enhance the flow of fog from the fog generator through the outer peripheral channels 1503, 1505.

The blocking member 1403 is configured to pivot between a blocking orientation (see FIG. 17) and a retracted orientation (see FIG. 18). As shown, in FIG. 17, in the closed orientation, the flow of fog through the inner peripheral channels 1703 is obstructed to enhance the flow of fog through the outer peripheral channels 1705, 1707. As such, a defect 1104 in the outer peripheral channel is more likely to be detected at the second end portion 205, for example, by the test apparatus 701 shown in FIG. 7. However, as the flow of fog is blocked through the inner peripheral channels 1703, inner defects 1511 associated with the inner channels cannot be detected by the test apparatus 701.

To detect the inner defects 1511, the blocking member 1403 can also be pivoted to an open orientation, as shown in FIG. 18, wherein fog is free to flow in all of the channels. As shown by arrows 1601, fog may be absorbed by the dry outer peripheral skin 1103 prior to reaching the defect 1104. As such, fog may not short circuit through the defect 1104 in sufficient quantities to be detected at the second end portion 205. However, as the central channels are not adjacent the outer peripheral skin 1103, absorption issues are not a concern. As such, as shown in FIG. 18, the fog entering the first end portion 203 may pass through the defect 1511 to allow the defect to be observed by the test apparatus 701 at the second end portion of the honeycomb filter 100.

As such, the test apparatus 701 can include a blocking apparatus 1401 that allows monitoring for defects associated with the inner peripheral channels 1703 when the blocking apparatus is oriented in the open orientation (see FIG. 18). The blocking apparatus 1401 can also allow for monitoring of defects associated with the outer peripheral channels 1705, 1707 when the blocking apparatus 1401 is oriented in the closed orientation shown in FIG. 17.

Figure 19:
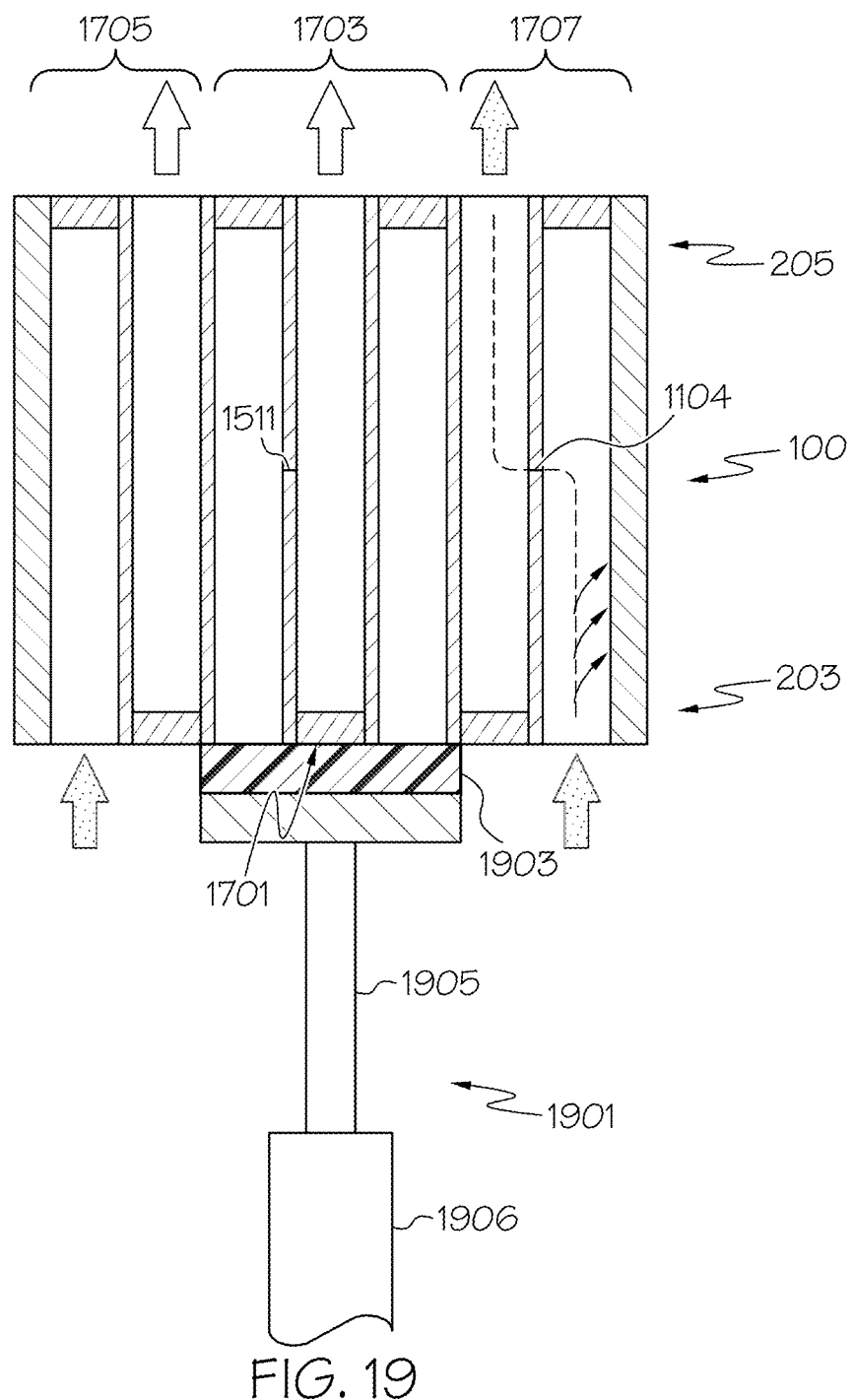
FIG. 19 illustrates a linear actuator being used to engage a blocking member with a central portion of the first end of the honeycomb filter.
Figure 20:
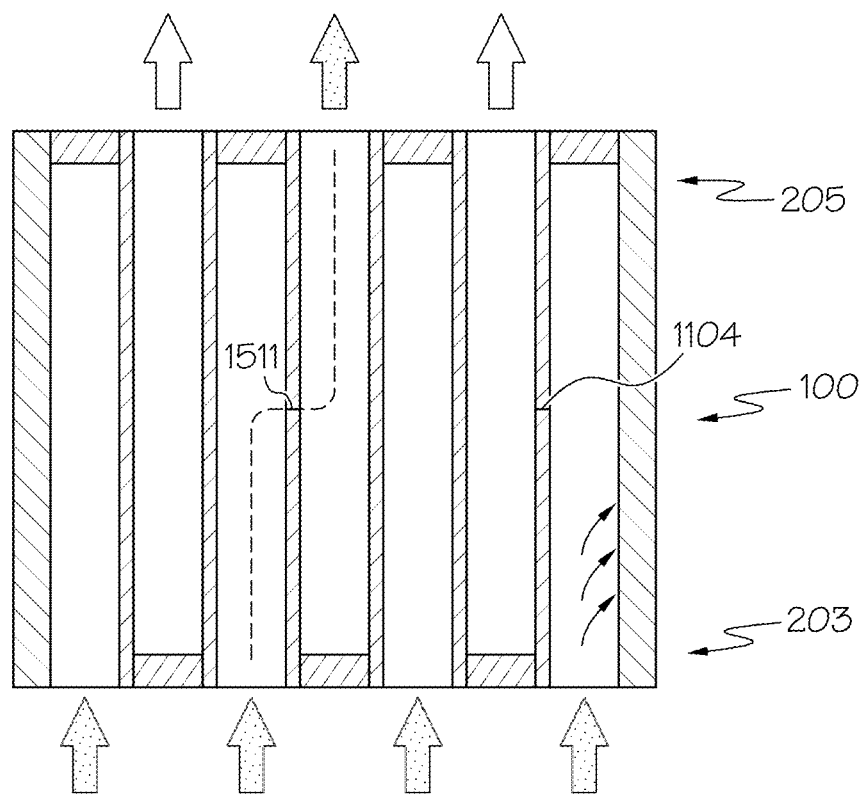
FIG. 20 illustrates the linear actuator of FIG. 19 being retracted to an open orientation.
Figure 20:
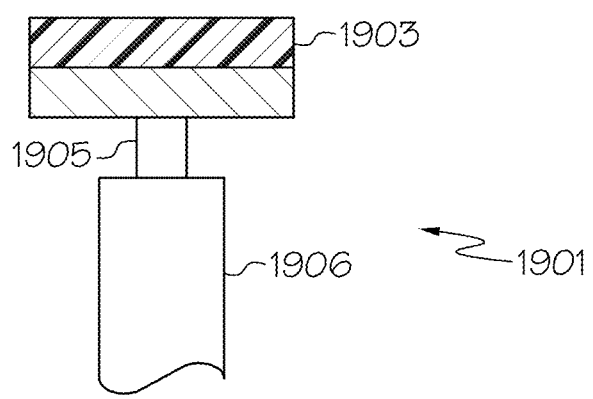

FIGS. 19 and 20 illustrate another example of a blocking apparatus 1901 that may be provided with a blocking member 1903 configured to engage a central portion 1701 of the first end portion 203 of the honeycomb filter 100 to enhance the flow of fog from the fog generator through the outer peripheral channels 1705, 1707. The blocking apparatus 1901 can comprise an piston 1905 extendable by a linear actuator 1906 configured to be extended to the closed orientation shown in FIG. 19 or retracted to the open orientation shown in FIG. 20. In the closed orientation shown in FIG. 19, defects in the outer peripheral channels 1705, 1707 may be detected in a similar manner as discussed with respect to FIG. 17 above. Likewise, in the open orientation shown in FIG. 20, defects in the inner peripheral channels 1703 can be detected in a similar manner as discussed with respect to FIG. 18 above. While the blocking apparatus 1901 is shown to engage the central portion 1701 of the first end portion 203, in further examples, a similar blocking apparatus may be oriented to engage a central portion of the second end portion 205.

Figure 21:
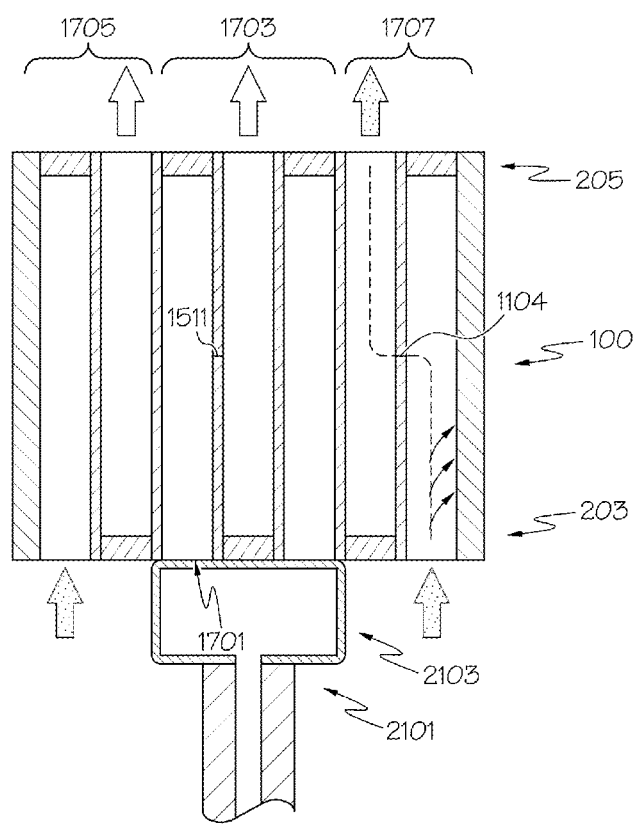
FIG. 21 illustrates an inflatable bladder being inflated to engage a central portion of the first end of the honeycomb filter.
Figure 22:
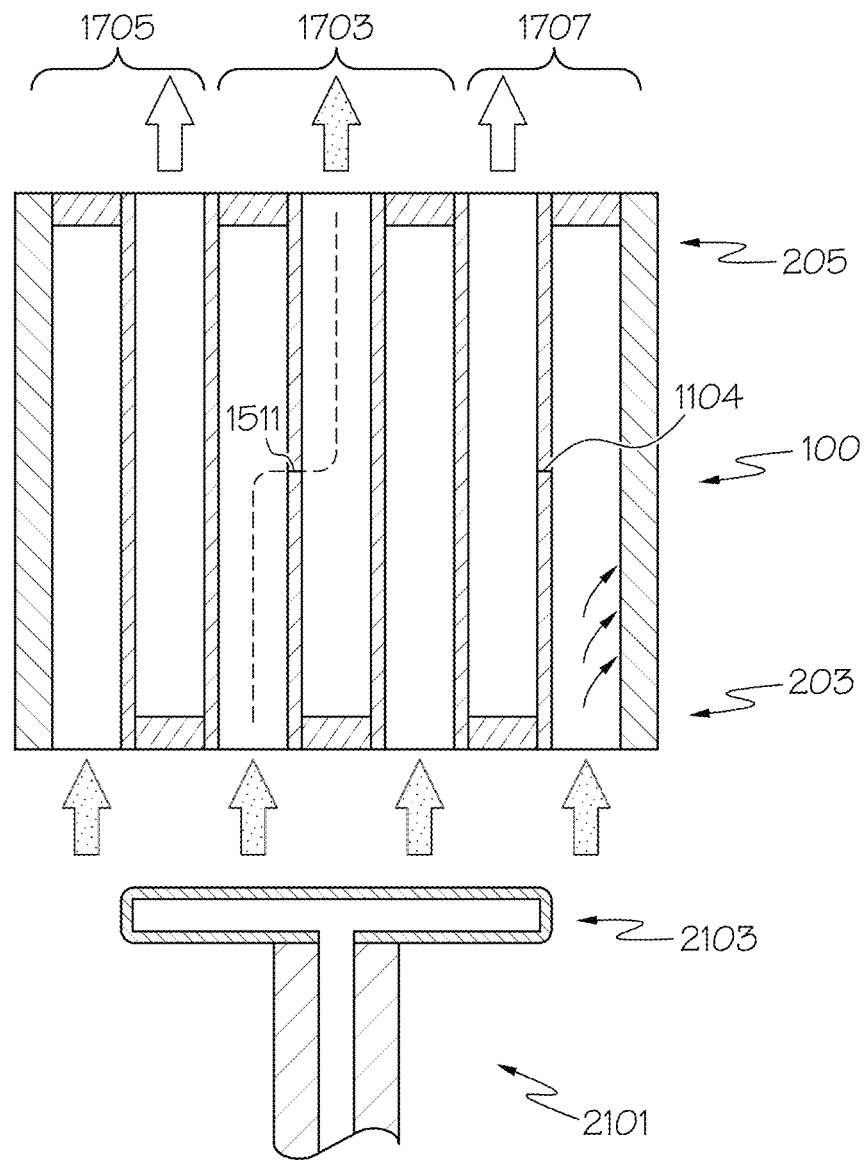
FIG. 22 illustrates the inflatable bladder being deflated to disengage the central portion of the first end of the honeycomb filter.

FIGS. 21 and 22 illustrate another example of a blocking apparatus 2101 that may be provided with a blocking member configured to engage a central portion 1701 of the first end portion 203 of the honeycomb filter 100 to enhance the flow of fog from the fog generator through the outer peripheral channels 1705, 1707. The blocking apparatus 2101 can comprise an inflatable bladder 2103 that may be inflated to be extended to a closed orientation shown in FIG. 21 or deflated to the open orientation shown in FIG. 22. In the closed orientation shown in FIG. 21, defects in the outer peripheral channels 1705, 1707 may be detected in a similar manner as discussed with respect to FIG. 17 above. Likewise, in the open orientation shown in FIG. 22, defects in the inner peripheral channels 1703 can be detected in a similar manner as discussed with respect to FIG. 18 above. While the blocking apparatus 2101 is shown to engage the central portion 1701 of the first end portion 203, in further examples, a similar blocking apparatus may be oriented to engage a central portion of the second end portion 205.

Figure 23:
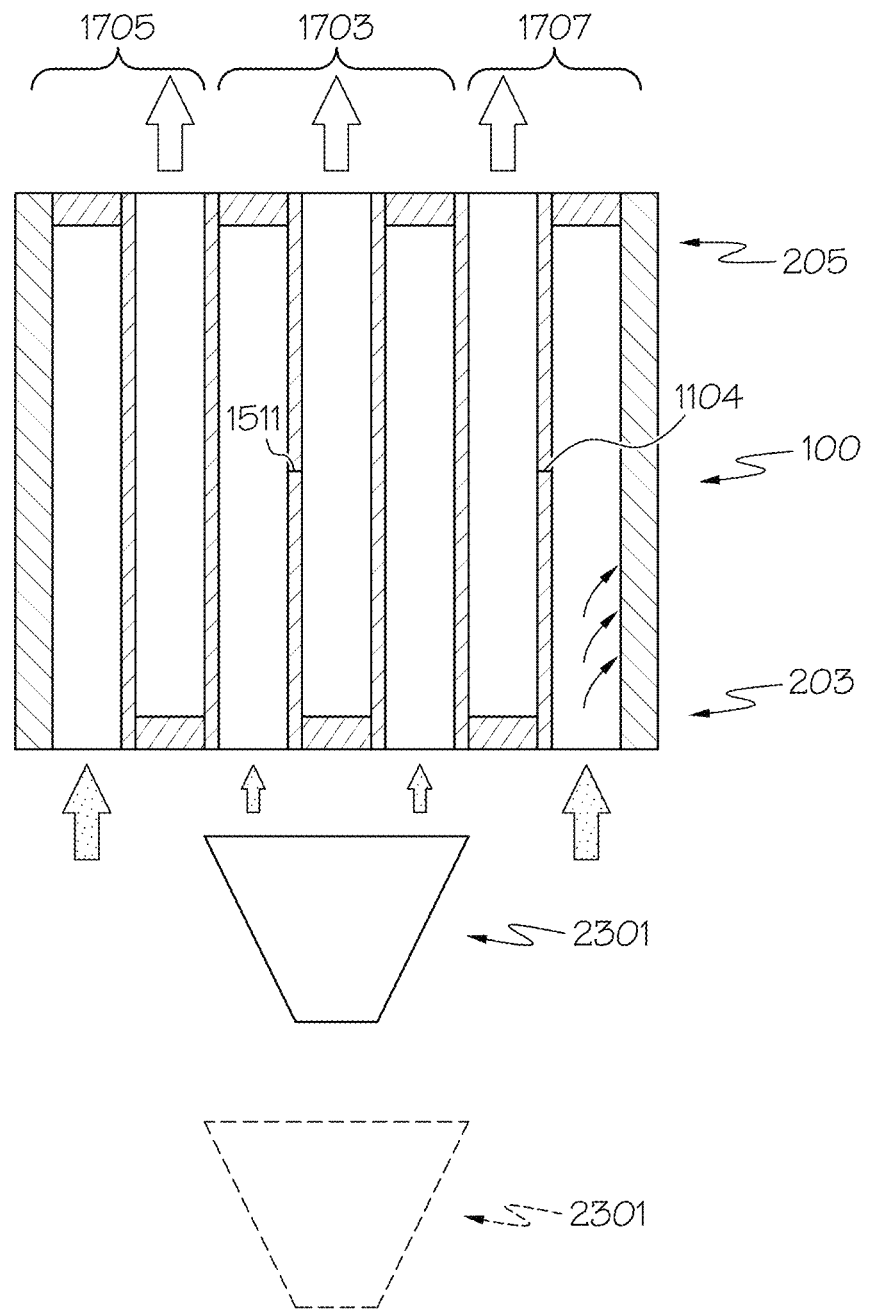
FIG. 23 illustrates a flow diverter being used to divert a flow of fog approaching the first end portion of the honeycomb filter.

FIG. 23 illustrates an example of a flow diverter 2301 that does not necessarily engage the honeycomb filter but may engage in further examples. Indeed, as shown in solid lines, the flow diverter 2301 may come close to the first end portion 203 of the honeycomb filter 100 without engaging. The flow diverter 2301 may comprise a solid conical member wherein fog flow may be diverted about the periphery of the flow diverter 2301 such that a greater quantity of fog is directed through the outer peripheral channels 1705, 1707 such that defects in the outer peripheral channels 1705, 1707 may be detected in a similar manner as discussed with respect to FIG. 17 above. Likewise, in the open orientation shown in dashed lines, defects in the inner peripheral channels 1703 can be detected in a similar manner as discussed with respect to FIG. 18 above.

Methods of testing the honeycomb filter 100 can therefore comprise the step of flowing fog with moisture droplets into the honeycomb network of channels at the first end portion 203 of the honeycomb filter 100. The method can further include the step of monitoring the second end portion 205 of the honeycomb filter 100 for moisture droplets of the fog exiting the honeycomb network of channels. The method can also include the step of obstructing a flow of fog through inner peripheral channels to enhance the flow of fog through the outer peripheral channels of the honeycomb network of channels.

As shown for example in FIGS. 17, 19 and 21, the method can include obstructing a flow of fog through the inner peripheral channels 1703 at the first end portion 203 of the honeycomb filter 100. As shown in FIG. 15, the method can also include the step of obstructing a flow of fog through the inner peripheral channels 1507 at the second end portion 205 of the honeycomb filter 100.

In some examples, the step of monitoring can occur prior to the step of obstructing. For example, as shown in FIGS. 16, 18, 20 and 22, monitoring may be initially carried out to help determine defects within the inner peripheral channels. In further examples, the step of monitoring can occur after the step of obstructing. For example, as shown in FIGS. 15, 17, 19, and 21, monitoring may be initially carried out to help determine defects within the outer peripheral channels. In still further examples, the monitoring may occur before and after the step of obstructing. For example, as shown in FIGS. 16, 18, 20 and 22, monitoring may be initially carried out to help determine defects within the inner peripheral channels. As shown in FIGS. 15, 17, 19, and 21, monitoring may be then be subsequently carried out to help determine defects within the outer peripheral channels. In still further examples, monitoring may be initially carried out to determine defects in the outer peripheral channels and then subsequently carried out to determine defects in the inner peripheral channels.

Methods of testing a honeycomb filter with the fog generator, such as a nebulizer can be carried out under various processing parameters to help increase the efficiency and capability to identify defects within the honeycomb filter. For example, modeling indicates that temperature significantly affects the particle size distribution of the fog due to water droplet evaporation and condensation which affects the detection quality of the nebulizer setup. In one example, the honeycomb filters 100 may be maintained at an average temperature within a range of from 10° C. to about 30° C., for example from about 10° C. to about 25° C., for example, from about 20° C. to about 23° C. Such temperature ranges can allow maintenance of the droplet size distribution which can help control the process accuracy. Air humidity can also affect quality of the nebulizer set up. In one example, methods include flowing a fog with moisture droplets into the honeycomb network of channels at the first end portion 203 of the honeycomb filter 100 wherein the fog has a relative humidity of at least 80%. Providing appropriate maintenance of the honeycomb filter temperature within the ranges above together with the fog including a relative humidity of at least 80% can help increase the effectiveness of the test procedure. As such, the method can further include the step of effectively monitoring the second end portion 205 of the honeycomb filter 100 for moisture droplets of the fog exiting the honeycomb network of channels.

In further examples the temperature of the fog can also be controlled to help enhance performance of the testing procedure. For instance, in one example, the method includes the step of flowing fog with a temperature within a range of from about 10° C. to about 30° C., for example from about 10° C. to about 25° C., for example from about 23° C. to about 25° C.

In some testing environments, it is recognized that surrounding environmental ambient temperatures can swing widely throughout the year, resulting in variation in time duration and results. Variation increases over 25° C. can make fog generation difficult. In some examples, the testing apparatus may be placed in a controlled environment to ensure the temperature does not exceed 25° C. For example, a control room may be provided with the testing apparatus, wherein the control room is maintained at a temperature that does not exceed 25° C. while the temperature outside of the control room may vary above the 25° C. threshold.

Still further, the moisture droplets of the fog can be controlled to help enhance the ability to identify defects in the filter. Based on unit filtration modeling data for a typical filter, as the droplet size of the fog becomes larger than 1 micron, it is more likely to be filtered out by the porous walls of an unflawed filter. On the other hand, droplets smaller than 1 micron may be able to navigate through the porous walls and provide a false reading of a defect within the filter. As such, in some examples, there is a desire to provide fog with droplets including a size of larger than 1 micron to allow the porous walls to effectively filter out the droplets when there is no defect present. Still further, the larger the droplet size, the interruption occurs with the light being used to illuminate any droplets emerging from the second end portion 205 of the honeycomb filter 100. Indeed, larger droplets will appear as brighter spots on the images. Very large droplet sizes may then have the benefit of being effectively filtered out by the porous walls while also being easily detected by imaging at the second end portion 20 of the honeycomb filter 100.

However, there is an upper limit imposed due to inertia of the particles flowing through the filter. As such, methods can provide fog with moisture droplets having a mean droplet size of from about 1 micron to about 25 microns, for example, from about 5 microns to about 25 microns, for example, from about 10 microns to about 15 microns. In some examples, it is possible to use larger droplets at lower relative humidity so that when the droplets flow, they will evaporate, thereby reducing the droplet size and increasing the humidity of the fog. Such droplet sizes are believed to be sufficient size for effective filtration by the porous walls without being so large that adverse flow conditions occur do to the inertia of the particles navigating through the defects in the walls of the honeycomb filter.

In still further examples, pressure differentials may be controlled between the first end portion and the second end portion to help provide adequate pressure drop to facilitate the testing procedure. In one example, the fog can have a pressure differential between the first end portion 203 and the second end portion 205 of the honeycomb filter 100 of from about 32 Pa to about 37 Pa. Such pressure differentials may help provide a desired flow of fog through the honeycomb network of channels. In one example, the channels have a flow rate of from about 0.075 m/sec to about 0.1 msec.

It will be apparent to those skilled in the art that various modifications and variations can be made to the described embodiments without departing from the spirit and scope of the claimed invention. Thus, it is intended that the present claimed invention cover the modifications and variations of the embodiments described herein provided they come within the scope of the appended claims and their equivalents.

What is claimed is:

1. A method of testing a honeycomb filter comprising the steps of:

(I) providing a honeycomb filter including a first end portion and a second end portion along an axis of the honeycomb filter, the honeycomb filter including honeycomb network of channels defined by a plurality of intersecting porous walls, wherein the honeycomb network of channels extend along the axis of the honeycomb filter between the first end portion and the second end portion;

(II) maintaining an average temperature of the honeycomb filter within a range of from about 10° C. to about 30° C.;

(III) flowing a fog with moisture droplets into the honeycomb network of channels at the first end portion of the honeycomb filter; and (IV) monitoring the second end portion of the honeycomb filter for moisture droplets of the fog exiting the honeycomb network of channels.

2. The method of claim 1, wherein step (III) flows the fog at a pressure differential between the first end portion and the second end portion of from about 32 Pa to about 37 Pa.

3. The method of claim 1, wherein step (III) flows the fog through honeycomb network of channels at a flow rate of from about 0.075 m/sec to about 0.1 m/sec.

4. The method of claim 1, wherein after step (I) and prior to step (II), further comprising wetting at least one of the first end portion and the second end portion to provide at least one wetted end portion, wherein the wetted end portion has a higher degree of wetness than an intermediate portion disposed between the first end portion and the second end portion.

5. The method of claim 1, wherein step (I) further includes providing the honeycomb filter with an outer peripheral surface circumscribing the honeycomb network of channels and extending between the first end portion and the second end portion, and the method further comprises wetting the outer peripheral surface of the honeycomb filter to enhance the flow of fog through outer peripheral channels of the honeycomb network of channels.

6. The method of claim 1, further comprising the step of blocking a flow of fog through inner peripheral channels of the honeycomb network of channels to enhance the flow of fog through outer peripheral channels of the honeycomb network of channels.

7. The method of claim 1, wherein the fog includes a relative humidity of at least 80%.

8. The method of claim 1, wherein step (II) maintains the average temperature of the honeycomb filter within a range of from about 10° C. to about 25° C.

9. The method of claim 8, wherein step (II) maintains the average temperature of the honeycomb filter within a range of from about 20° C. to about 23° C.

10. The method of claim 1, wherein step (III) flows the fog with the moisture droplets having a mean droplet size of from about 1 micron to about 25 microns.

11. The method of claim 10, wherein step (III) flows the fog with the moisture droplets having a mean droplet size of from about 5 microns to about 25 microns.

12. The method of claim 1, wherein step (III) flows the fog with a temperature within a range of from about 10° C. to about 30° C.

13. The method of claim 12, wherein step (III) flows the fog with a temperature within a range of from about 10° C. to about 25° C.

14. The method of claim 13, wherein step (III) flows the fog with a temperature within a range of from about 23° C. to about 25° C.

15. A method of testing a honeycomb filter comprising the steps of:
 (I) providing a honeycomb filter including a first end portion and a second end portion along an axis of the honeycomb filter, the honeycomb filter including honeycomb network of channels defined by a plurality of intersecting porous walls, wherein the honeycomb network of channels extend along the axis of the honeycomb filter between the first end portion and the second end portion;
 (II) flowing a fog with moisture droplets into the honeycomb network of channels at the first end portion of the honeycomb filter, and the fog including a temperature within a range of from about 10° C. to about 30° C.; and
 (III) monitoring the second end portion of the honeycomb filter for moisture droplets of the fog exiting the honeycomb network of channels.

16. The method of claim 15, wherein step (III) flows the fog at a pressure differential between the first end portion and the second end portion of from about 32 Pa to about 37 Pa.

17. The method of claim 15, wherein step (III) flows the fog through honeycomb network of channels at a flow rate of from about 0.075 m/sec to about 0.1 m/sec.

18. The method of claim 15, wherein after step (I) and prior to step (II), further comprising wetting at least one of the first end portion and the second end portion to provide at least one wetted end portion, wherein the wetted end portion has a higher degree of wetness than an intermediate portion disposed between the first end portion and the second end portion.

19. The method of claim 15, wherein step (I) further includes providing the honeycomb filter with an outer peripheral surface circumscribing the honeycomb network of channels and extending between the first end portion and the second end portion, and the method further comprises wetting the outer peripheral surface of the honeycomb filter to enhance the flow of fog through outer peripheral channels of the honeycomb network of channels.

20. The method of claim 15, further comprising the step of blocking a flow of fog through inner peripheral channels of the honeycomb network of channels to enhance the flow of fog through outer peripheral channels of the honeycomb network of channels.

21. The method of claim 15, wherein the fog includes a relative humidity of at least 80%.

22. The method of claim 15, wherein step (II) flows the fog with a temperature within a range of from about 10° C. to about 25° C.

23. The method of claim 22, wherein step (II) flows the fog with a temperature within an range of from about 23° C. to about 25° C.

24. The method of claim 15, wherein step (III) flows the fog with the moisture droplets having a mean droplet size of from about 1 micron to about 25 microns.

25. The method of claim 24, wherein step (III) flows the fog with the moisture droplets having a mean droplet size of from about 5 microns to about 25 microns.

26. A method of testing a honeycomb filter comprising the steps of:
 (I) providing a honeycomb filter including a first end portion and a second end portion along an axis of the honeycomb filter, the honeycomb filter including honeycomb network of channels defined by a plurality of intersecting porous walls, wherein the honeycomb network of channels extend along the axis of the honeycomb filter between the first end portion and the second end portion;
 (II) maintaining an average temperature of the honeycomb filter within a range of from about 10° C. to about 30° C.;
 (III) flowing a fog with moisture droplets into the honeycomb network of channels at the first end portion of the honeycomb filter, the moisture droplets having a mean droplet size of from about 5 microns to about 25 microns, and the fog including a temperature within a range of from about 10° C. to about 30° C.; and
 (IV) monitoring the second end portion of the honeycomb filter for moisture droplets of the fog exiting the honeycomb network of channels.

27. The method of claim 26, wherein step (III) flows the fog at a pressure differential between the first end portion and the second end portion of from about 32 Pa to about 37 Pa.

28. The method of claim 26, wherein step (III) flows the fog through honeycomb network of channels at a flow rate of from about 0.075 m/sec to about 0.1 msec.

29. The method of claim 26, wherein after step (I) and prior to step (II), further comprising wetting at least one of the first end portion and the second end portion to provide at least one wetted end portion, wherein the wetted end portion has a higher degree of wetness than an intermediate portion disposed between the first end portion and the second end portion.

30. The method of claim 26, wherein step (I) further includes providing the honeycomb filter with an outer peripheral surface circumscribing the honeycomb network of channels and extending between the first end portion and the second end portion, and the method further comprises wetting the outer peripheral surface of the honeycomb filter to enhance the flow of fog through outer peripheral channels of the honeycomb network of channels.

31. The method of claim 26, further comprising the step of blocking a flow of fog through inner peripheral channels of the honeycomb network of channels to enhance the flow of fog through outer peripheral channels of the honeycomb network of channels.

32. The method of claim 26, wherein the fog includes a relative humidity of at least 80%.

* * * * *